United States Patent
Warren et al.

(10) Patent No.: US 9,636,514 B2
(45) Date of Patent: May 2, 2017

(54) ADAPTIVE CONFIRMATION OF TREATABLE ARRHYTHMIA IN IMPLANTABLE CARDIAC STIMULUS DEVICES

(71) Applicant: CAMERON HEALTH, INC., St. Paul, MN (US)

(72) Inventors: Jay A. Warren, San Juan Capistrano, CA (US); Rick Sanghera, San Clemente, CA (US); Venugopal Allavatam, Maple Grove, MN (US)

(73) Assignee: Cameron Health, Inc., St. Paul, MN (US)

(*) Notice: Subject to any disclaimer, the term of this patent is extended or adjusted under 35 U.S.C. 154(b) by 0 days.

(21) Appl. No.: 14/852,701

(22) Filed: Sep. 14, 2015

(65) Prior Publication Data
US 2015/0375004 A1    Dec. 31, 2015

Related U.S. Application Data

(63) Continuation of application No. 12/826,241, filed on Jun. 29, 2010, now Pat. No. 9,149,637.

(60) Provisional application No. 61/221,316, filed on Jun. 29, 2009.

(51) Int. Cl.
*A61N 1/39* (2006.01)
*A61B 5/0464* (2006.01)
*A61N 1/362* (2006.01)

(52) U.S. Cl.
CPC .......... *A61N 1/3987* (2013.01); *A61B 5/0464* (2013.01); *A61N 1/3622* (2013.01); *A61N 1/3925* (2013.01); *A61N 1/3956* (2013.01); *A61N 1/3943* (2013.01)

(58) Field of Classification Search
None
See application file for complete search history.

(56) References Cited

U.S. PATENT DOCUMENTS

| | | | |
|---|---|---|---|
| 4,184,493 A | 1/1980 | Langer et al. | |
| 4,300,567 A | 11/1981 | Kolenik et al. | |
| 4,407,288 A | 10/1983 | Langer et al. | |
| 4,450,527 A | 5/1984 | Sramek | |
| 4,457,315 A | 7/1984 | Bennish | |
| 4,595,009 A | 6/1986 | Leinders | |
| 4,679,144 A | 7/1987 | Cox et al. | |

(Continued)

FOREIGN PATENT DOCUMENTS

| | | |
|---|---|---|
| EP | 0554208 A2 | 8/1993 |
| EP | 2459275 A1 | 6/2012 |

(Continued)

OTHER PUBLICATIONS

"Australian Application Serial No. 2010273710, Voluntary Amendment filed Jan. 16, 2012," 5 pgs.

(Continued)

*Primary Examiner* — Erica Lee
(74) *Attorney, Agent, or Firm* — Seager, Tufte & Wickhem LLP

(57) ABSTRACT

Methods and devices for adjusting therapy delivery decisions in an implantable cardiac stimulus device. Some example methods and devices use a first counter to track benign cardiac activity during therapy preparations and a second counter to track shockable cardiac activity once therapy is ready. Therapy can then be delivered if or when the second counter exceeds the first counter.

20 Claims, 12 Drawing Sheets

(56) References Cited

U.S. PATENT DOCUMENTS

| | | |
|---|---|---|
| 4,693,253 A | 9/1987 | Adams |
| 4,750,494 A | 6/1988 | King |
| 4,779,617 A | 10/1988 | Whigham |
| 4,979,110 A | 12/1990 | Albrecht et al. |
| 4,989,602 A | 2/1991 | Sholder et al. |
| 5,000,189 A | 3/1991 | Throne et al. |
| 5,105,810 A | 4/1992 | Collins et al. |
| 5,179,945 A | 1/1993 | Van Hofwegen et al. |
| 5,184,616 A | 2/1993 | Weiss |
| 5,188,105 A | 2/1993 | Keimel |
| 5,190,034 A | 3/1993 | Sholder |
| 5,191,884 A | 3/1993 | Gilli et al. |
| 5,193,535 A | 3/1993 | Bardy et al. |
| 5,215,098 A | 6/1993 | Steinhaus et al. |
| 5,217,021 A | 6/1993 | Steinhaus et al. |
| 5,251,625 A | 10/1993 | Wilson et al. |
| 5,257,621 A | 11/1993 | Bardy et al. |
| 5,271,411 A | 12/1993 | Ripley et al. |
| 5,280,792 A | 1/1994 | Leong et al. |
| 5,299,119 A | 3/1994 | Kraf et al. |
| 5,313,953 A | 5/1994 | Yomtov et al. |
| 5,330,504 A | 7/1994 | Somerville et al. |
| 5,331,966 A | 7/1994 | Bennett et al. |
| 5,342,402 A | 8/1994 | Olson et al. |
| 5,342,407 A | 8/1994 | Dahl et al. |
| 5,351,696 A | 10/1994 | Riff et al. |
| 5,376,104 A | 12/1994 | Sakai et al. |
| 5,423,326 A | 6/1995 | Wang et al. |
| 5,447,519 A | 9/1995 | Peterson |
| 5,464,430 A | 11/1995 | Rossing |
| 5,464,431 A | 11/1995 | Adams et al. |
| 5,522,852 A | 6/1996 | White et al. |
| 5,534,019 A | 7/1996 | Paspa |
| 5,545,186 A | 8/1996 | Olson et al. |
| 5,558,098 A | 9/1996 | Fain |
| 5,607,455 A | 3/1997 | Armstrong |
| 5,658,317 A | 8/1997 | Haefner et al. |
| 5,709,215 A | 1/1998 | Perttu et al. |
| 5,755,736 A | 5/1998 | Gillberg et al. |
| 5,766,225 A | 6/1998 | Kramm |
| 5,792,192 A | 8/1998 | Lu |
| 5,817,134 A | 10/1998 | Greenhut et al. |
| 5,827,197 A | 10/1998 | Bocek et al. |
| 5,857,977 A | 1/1999 | Caswell et al. |
| 5,991,657 A | 11/1999 | Kim |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,095,987 A | 8/2000 | Shmulewitz et al. |
| 6,115,628 A | 9/2000 | Stadler et al. |
| 6,144,879 A | 11/2000 | Gray |
| 6,148,230 A | 11/2000 | KenKnight |
| 6,169,923 B1 | 1/2001 | Kroll |
| 6,223,078 B1 | 4/2001 | Marcovecchio |
| 6,230,055 B1 | 5/2001 | Sun et al. |
| 6,236,882 B1 | 5/2001 | Lee et al. |
| 6,240,313 B1 | 5/2001 | Esler |
| 6,266,554 B1 | 7/2001 | Hsu et al. |
| 6,280,462 B1 | 8/2001 | Hauser et al. |
| 6,308,095 B1 | 10/2001 | Hsu et al. |
| 6,334,071 B1 | 12/2001 | Lu |
| 6,377,844 B1 | 4/2002 | Graen |
| 6,381,493 B1 | 4/2002 | Stadler et al. |
| 6,393,316 B1 | 5/2002 | Gillberg et al. |
| 6,397,100 B2 | 5/2002 | Stadler et al. |
| 6,411,844 B1 | 6/2002 | Kroll et al. |
| 6,438,410 B2 | 8/2002 | Hsu et al. |
| 6,449,503 B1 | 9/2002 | Hsu |
| 6,493,579 B1 | 12/2002 | Gilkerson et al. |
| 6,493,584 B1 | 12/2002 | Lu |
| 6,505,068 B2 | 1/2003 | Bonnet et al. |
| 6,516,225 B1 | 2/2003 | Florio |
| 6,561,984 B1 | 5/2003 | Turcott |
| 6,567,691 B1 | 5/2003 | Stadler |
| 6,574,505 B1 | 6/2003 | Warren |
| 6,575,912 B1 | 6/2003 | Turcott |
| 6,587,720 B2 | 7/2003 | Hsu et al. |
| 6,625,490 B1 | 9/2003 | McClure et al. |
| 6,643,549 B1 | 11/2003 | Bradley et al. |
| 6,647,292 B1 | 11/2003 | Bardy et al. |
| 6,684,100 B1 | 1/2004 | Sweeney et al. |
| 6,699,200 B2 | 3/2004 | Cao et al. |
| 6,708,058 B2 | 3/2004 | Kim et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,745,068 B2 | 6/2004 | Koyrakh et al. |
| 6,754,528 B2 | 6/2004 | Bardy et al. |
| 6,889,079 B2 | 5/2005 | Bocek et al. |
| 6,909,916 B2 | 6/2005 | Spinelli et al. |
| 6,950,702 B2 | 9/2005 | Sweeney |
| 7,016,730 B2 | 3/2006 | Ternes |
| 7,020,523 B1 | 3/2006 | Lu et al. |
| 7,027,856 B2 | 4/2006 | Zhou et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,062,314 B2 | 6/2006 | Zhu et al. |
| 7,062,315 B2 | 6/2006 | Koyrakh et al. |
| 7,062,322 B2 | 6/2006 | Stadler et al. |
| 7,076,289 B2 | 7/2006 | Sarkar et al. |
| 7,085,599 B2 | 8/2006 | Kim et al. |
| 7,117,035 B2 | 10/2006 | Wagner et al. |
| 7,149,575 B2 | 12/2006 | Ostroff et al. |
| 7,162,301 B2 | 1/2007 | Kim et al. |
| 7,167,747 B2 | 1/2007 | Gunderson et al. |
| 7,184,815 B2 | 2/2007 | Kim et al. |
| 7,184,818 B2 | 2/2007 | Kim et al. |
| 7,191,004 B2 | 3/2007 | Kim et al. |
| 7,194,302 B2 | 3/2007 | Bardy et al. |
| 7,218,966 B2 | 5/2007 | Haefner |
| 7,236,819 B2 | 6/2007 | Brockway et al. |
| 7,248,921 B2 | 7/2007 | Palreddy et al. |
| 7,266,409 B2 | 9/2007 | Gunderson |
| 7,283,863 B2 | 10/2007 | Gunderson |
| 7,302,294 B2 | 11/2007 | Kamath et al. |
| 7,330,757 B2 | 2/2008 | Ostroff et al. |
| 7,346,392 B2 | 3/2008 | KenKnight |
| 7,376,458 B2 | 5/2008 | Palreddy et al. |
| 7,379,772 B2 | 5/2008 | Bardy et al. |
| 7,386,342 B1 | 6/2008 | Falkenberg et al. |
| 7,392,085 B2 | 6/2008 | Warren et al. |
| 7,444,182 B2 | 10/2008 | Ostroff et al. |
| 7,447,540 B1 | 11/2008 | Nabutovsky et al. |
| 7,467,009 B2 | 12/2008 | Palreddy et al. |
| 7,477,935 B2 | 1/2009 | Palreddy et al. |
| 7,496,408 B2 | 2/2009 | Ghanem et al. |
| 7,496,409 B2 | 2/2009 | Greenhut et al. |
| 7,499,750 B2 | 3/2009 | Haefner et al. |
| 7,522,959 B2 | 4/2009 | Hauser et al. |
| 7,546,159 B1 | 6/2009 | Nabutovsky et al. |
| 7,555,335 B2 | 6/2009 | Kamath et al. |
| 7,559,900 B2 | 7/2009 | Gillberg |
| 7,567,835 B2 | 7/2009 | Gunderson et al. |
| 7,570,997 B2 | 8/2009 | Lovett et al. |
| 7,593,771 B2 | 9/2009 | Yonce et al. |
| 7,623,913 B2 | 11/2009 | Phillips |
| 7,623,916 B2 | 11/2009 | Julian |
| 7,655,014 B2 | 2/2010 | Ko et al. |
| 7,682,316 B2 | 3/2010 | Anderson et al. |
| 7,684,864 B2 | 3/2010 | Olson et al. |
| 7,715,906 B2 | 5/2010 | Krause et al. |
| 7,734,345 B2 | 6/2010 | Cinbis |
| 7,761,142 B2 | 7/2010 | Ghanem et al. |
| 7,774,049 B2 | 8/2010 | Ghanem et al. |
| 7,783,354 B2 | 8/2010 | Gunderson |
| 7,797,036 B2 | 9/2010 | Zhang et al. |
| 7,865,233 B2 | 1/2011 | Haefner |
| 7,894,894 B2 | 2/2011 | Stadler et al. |
| 7,904,142 B2 | 3/2011 | Kim et al. |
| 7,904,153 B2 | 3/2011 | Greenhut et al. |
| 7,907,993 B2 | 3/2011 | Ghanem et al. |

(56) References Cited

U.S. PATENT DOCUMENTS

| | | |
|---|---|---|
| 2003/0114888 A1 | 6/2003 | Stadler et al. |
| 2004/0215239 A1 | 10/2004 | Favet et al. |
| 2004/0215240 A1 | 10/2004 | Lovett et al. |
| 2004/0220628 A1 | 11/2004 | Wagner |
| 2004/0230229 A1 | 11/2004 | Lovett et al. |
| 2005/0107838 A1 | 5/2005 | Lovett et al. |
| 2005/0131464 A1 | 6/2005 | Heinrich et al. |
| 2005/0154421 A1 | 7/2005 | Ousdigian |
| 2006/0122676 A1 | 6/2006 | Ko et al. |
| 2006/0167502 A1 | 7/2006 | Haefner |
| 2006/0167503 A1 | 7/2006 | Warren et al. |
| 2006/0167504 A1 | 7/2006 | Warren et al. |
| 2006/0241701 A1 | 10/2006 | Markowitz et al. |
| 2007/0032829 A1 | 2/2007 | Ostroff |
| 2007/0049975 A1 | 3/2007 | Cates et al. |
| 2007/0135847 A1 | 6/2007 | KenKnight |
| 2007/0142736 A1 | 6/2007 | Cazares et al. |
| 2007/0156190 A1 | 7/2007 | Cinbis et al. |
| 2007/0179539 A1 | 8/2007 | Degroot et al. |
| 2007/0179540 A1 | 8/2007 | Stegemann et al. |
| 2007/0232944 A1 | 10/2007 | Ghanem et al. |
| 2007/0232945 A1 | 10/2007 | Kleckner et al. |
| 2007/0232948 A1 | 10/2007 | Stadler et al. |
| 2007/0233198 A1 | 10/2007 | Ghanem et al. |
| 2007/0276445 A1 | 11/2007 | Sanghera et al. |
| 2008/0009906 A1 | 1/2008 | Perschbacher et al. |
| 2008/0015647 A1 | 1/2008 | Palreddy et al. |
| 2008/0077030 A1 | 3/2008 | Ostroff et al. |
| 2008/0086174 A1 | 4/2008 | Libbus et al. |
| 2008/0091242 A1 | 4/2008 | Kamath et al. |
| 2008/0132965 A1 | 6/2008 | Ostroff et al. |
| 2008/0161870 A1 | 7/2008 | Gunderson |
| 2008/0172098 A1 | 7/2008 | Gunderson |
| 2008/0183085 A1 | 7/2008 | Van Oort et al. |
| 2008/0188901 A1 | 8/2008 | Sanghera et al. |
| 2008/0215110 A1 | 9/2008 | Gunderson |
| 2008/0221632 A1 | 9/2008 | Bardy et al. |
| 2008/0228093 A1 | 9/2008 | Dong et al. |
| 2008/0243200 A1 | 10/2008 | Scinicariello et al. |
| 2008/0262559 A1 | 10/2008 | Zhang et al. |
| 2008/0275516 A1 | 11/2008 | Ghanem et al. |
| 2008/0275517 A1 | 11/2008 | Ghanem et al. |
| 2008/0275519 A1 | 11/2008 | Ghanem et al. |
| 2008/0275521 A1 | 11/2008 | Warren et al. |
| 2009/0018595 A1 | 1/2009 | Bharmi et al. |
| 2009/0036788 A1 | 2/2009 | Nabutovsky et al. |
| 2009/0043352 A1 | 2/2009 | Brooke et al. |
| 2009/0054796 A1 | 2/2009 | Sanghera et al. |
| 2009/0054938 A1 | 2/2009 | Ostroff et al. |
| 2009/0093731 A1 | 4/2009 | Palreddy et al. |
| 2009/0131998 A1 | 5/2009 | Warren et al. |
| 2009/0156957 A1 | 6/2009 | Linder et al. |
| 2009/0157128 A1 | 6/2009 | Seim et al. |
| 2009/0157132 A1 | 6/2009 | Linder et al. |
| 2009/0157137 A1 | 6/2009 | Gilkerson et al. |
| 2009/0228057 A1 | 9/2009 | Allavatam et al. |
| 2009/0240157 A1 | 9/2009 | Lian et al. |
| 2009/0240300 A1 | 9/2009 | Lian et al. |
| 2009/0259271 A1 | 10/2009 | Allavatam et al. |
| 2010/0004713 A1 | 1/2010 | Warren et al. |
| 2010/0106209 A1 | 4/2010 | Gunderson et al. |

FOREIGN PATENT DOCUMENTS

| | | |
|---|---|---|
| JP | 2005512629 A | 5/2005 |
| JP | 2006524106 A | 10/2006 |
| JP | 2005414092 A | 11/2006 |
| JP | 2008528103 A | 7/2008 |
| JP | 2012532633 A | 12/2012 |
| WO | 2011008550 A1 | 1/2011 |

OTHER PUBLICATIONS

"Chinese Application Serial No. 201080038609.8, Office Action mailed Dec. 6, 2013," With English Translation, 21 pgs.

"International Application Serial No. PCT/US2010/040419, International Preliminary Report on Patentability mailed Jan. 12, 2012," 11 pgs.

"International Application Serial No. PCT/US2010/040419, International Preliminary Report on Patentability mailed Nov. 10, 2010," 4 pgs.

"International Application Serial No. PCT/US2010/040419, International Preliminary Report on Patentability mailed Nov. 10, 2010", 9 pgs.

"Japanese Application Serial No. 2012-517859, Office Action mailed May 7, 2014," With English Translation, 5 pgs.

"Japanese Application Serial No. 2012-517859, Response filed Aug. 7, 2014 to Office Action mailed May 7, 2014," With English Translation, 10 pgs.

Allavatam et al., U.S. Appl. No. 61/255,253, filed Oct. 27, 2009.

Gunderson et al., "An Algorithm to Predict Implantable Cardioverter-Defibrillator Lead Failure." JACC, Nov. 2004, 44:9, pp. 1898-1902.

Olson et al., "Onset and Stability for Ventricular Tachyarrhythmia Detection in an Implantable Pacer-Cardioverter-Defibrillator." IEEE, (1987) pp. 167-170.

Schuder, "The Role of an Engineering Oriented Medical Research Group in Developing Improved Methods and Devices for Achieving Ventricular Defibrillation: The University of Missouri Experience." PACE, 16, Jan. 1993, pp. 95-124.

Schwake et al., "Komplikationen nit Sonden bei 340 Patienten mit einem Implantierbaren Kardioverter/Defibrillator." Z Kardiol (1999) 88:8 pp. 559-565.

Swerdlow et al., "Advanced ICD Troubleshooting: Part I." Online article at http://www.medscape.com/viewarticle/520588_print, accessed and printed Jul. 7, 2009, indicates publication Jan. 9, 2006 (not confirmed).

Throne, "A Comparison of Four New Time-Domain Techniques for Discriminating Monomorphic Ventricular Tachycardia from Sinus Rhythm Using Ventricular Waveform Morphology." IEEE Transactions on Biomedical Engineering 38:6 pp. 561-570, Jun. 1991.

All non-patent literature documents and foreign patent documents have been previously uploaded in parent U.S. Appl. No. 12/826,241.

ADAPTIVE CONFIRMATION OF TREATABLE ARRHYTHMIA IN IMPLANTABLE CARDIAC STIMULUS DEVICES

RELATED APPLICATIONS

The present application is a continuation of U.S. patent application Ser. No. 12/826,241, filed Jun. 29, 2010, now U.S. Pat. No. 9,149,637, which claims the benefits of and priority to U.S. Provisional Patent Application No. 61/221,316, titled CONFIRMATION OF TREATABLE ARRHYTHMIA IN IMPLANTABLE CARDIAC STIMULUS DEVICES, filed 29 Jun. 2009, and the entire disclosure of which is incorporated herein by reference.

FIELD

The present invention relates generally to implantable medical device systems that sense and analyze cardiac signals. More particularly, the present invention relates to implantable medical devices that analyze cardiac signals in order to classify cardiac activity as likely benign or treatable.

BACKGROUND

An implantable cardiac stimulus device (ICSD) typically senses cardiac electrical signals in an implantee and uses the sensed signals to classify the implantee's cardiac rhythm as normal/benign or treatable/malignant. Illustrative treatable arrhythmias may include ventricular fibrillation and/or ventricular tachyarrhythmia. Other rhythms may also be considered "treatable" depending upon patient characteristics and physician preferences.

If a treatable arrhythmia is identified and defibrillation or cardioversion is to be delivered, an ICSD typically needs some period of time to prepare for therapy delivery. For example, a three, six or nine-volt battery supply may be used to provide hundreds or even thousands of volts of stimulus amplitude by charging a capacitor for several seconds using a charging circuit. As a result, once a treatable condition is identified, there is a charging time period corresponding to the preparations of the device to deliver therapy. Anti-tachycardia pacing (ATP) may not require such a charging delay, however, to ensure that therapy is appropriate, a system delivering ATP may include a delay for confirmation of arrhythmia before therapy delivery.

Some treatable arrhythmias may be intermittent or may spontaneously revert to a benign rhythm. If an apparently treatable arrhythmia spontaneously reverts to a benign rhythm, therapy becomes unnecessary. In general, therapy delivery should be managed to avoid unnecessary therapies.

To avoid unnecessary therapy, devices may perform rhythm confirmation just before delivering therapy. New or alternative methods for managing delivery through therapy confirmation are desired.

SUMMARY

A first illustrative embodiment is a method of patient treatment using an implantable cardiac stimulus device (ICSD). The first embodiment may be performed in the context of a system that has made an initial identification of a treatable condition. In the example, after the initial identification of a treatable condition, cardiac activity is monitored to identify indications of a reversion to benign cardiac rhythm while the ICSD prepares to deliver therapy. Once the ICSD is prepared to deliver therapy, analysis is performed to confirm whether/when therapy should be delivered. If indications of a reversion to benign cardiac rhythm are identified, therapy confirmation analysis is adjusted to delay therapy delivery in order to avoid delivering therapy into a benign rhythm. If benign cardiac rhythm persists, the therapy delivery may also be cancelled. In some examples, the ICSD prepares to deliver therapy by, for example, transferring data to memory, recording sensed signals, establishing a wait period in terms of time or detected events, identifying synchronization data and/or other functions. In some embodiments and ICSD prepares for therapy delivery by charging a therapy delivery capacitor to a desired energy/voltage, though this is not always part of the preparation.

In one example, initial treatable condition criteria is/are applied to determine whether to advance to confirmation methods, and different criteria are applied for confirmation. In one illustrative example, intervals between detected events are analyzed to use rate as criteria for initial identification and confirmation. In further examples, morphology and/or combinations of interval analysis and morphology may be used to identify indications of benign or treatable arrhythmias. In some examples, one of rate or morphology is used for initial identification, and the other or a combination of rate and morphology can be used for confirmation. Indications of benign conditions can be tracked and quantified after the initial identification of a treatable condition and are then used in the confirmation step to delay therapy delivery.

In another embodiment, a method of patient treatment in an ICSD applies a set of criteria to determine whether a treatable condition appears likely. Once an initial treatable condition is identified, the data that led to the initial identification is cleared and confirmatory criteria are applied. If the confirmatory criteria are met, therapy is delivered. In one such example, an X/Y counter is used to analyze a window of data for the initial treatable condition identification, and the X/Y counter is cleared and re-filled for applying confirmatory criteria.

In another embodiment, an X/Y counter is used to generate an initial analysis of treatable condition. Upon an initial finding of a treatable condition, the values in the X/Y counter are stored, and analysis continues to fill the X/Y counter with new data. A confirmation step is then performed when the status of the X/Y counter is compared to the status stored after the initial analysis. In the example, therapy will be delivered once the X/Y counter reaches a status that is at least equivalent to that which occurred at the time of initial analysis.

The ICSD may be configured to deliver therapy such as cardioversion or defibrillation that calls for a charging time during which a therapy capacitor is charged to a desired level for therapy. If so, and in several examples, the device begins charging to prepare for therapy delivery upon identification of the initial treatable condition. For some such examples, the confirmation analysis may include checking whether preparation for therapy delivery is complete as well as analyzing data sensed before, during or after charging began or finished. The invention is not limited to analysis during/following initiation of capacitor charging, as, for example, some therapies (such as ATP) may not require capacitor charging. For example, preparation for therapy can follow the initial identification of treatable condition by including a delay period defined in terms of a time delay or a number of detected events; part of the "preparation" includes simply waiting to ensure accuracy of the decision-making process.

Additional embodiments include devices and systems configured or adapted to perform the above methods. The present invention can be embodied in a large number of different examples, only a few of which are summarized here in this "Summary". Further examples are shown below in the "Detailed Description."

DETAILED DESCRIPTION

The following detailed description should be read with reference to the drawings. The drawings, which are not necessarily to scale, depict illustrative embodiments and are not intended to limit the scope of the invention. Some of the following examples and explanations include references to issued patents and pending patent applications. These references are for illustrative purposes and are not intended to limit the present invention to the particular methods or structures from the referenced patents and patent applications.

Unless implicitly required or explicitly stated, the methods below do not require any particular order of steps. It should be understood that when the following examples refer to a "current event," in some embodiments, this means the most recently detected cardiac event is being analyzed. However, this need not be the case, and some embodiments perform analysis that is delayed by one or more detections and or a fixed period of time. Choices shown regarding use of rectified or unrectified signals are merely illustrative, and may be changed if desired.

Several embodiments disclosed herein can be used in an implantable cardiac stimulus device (ICSD). One particular type of ICSD is an implantable cardioverter-defibrillator, which typically provides therapy in the form of cardioversion and/or defibrillation therapies and, when needed/programmed, anti-bradycardia pacing. An ICSD may provide anti-tachycardia pacing, for example in a tiered therapy system, as well as other functionality including but not limited to other pacing therapies or any other suitable therapy. An ICSD may also treat atrial arrhythmias.

Figure 1:
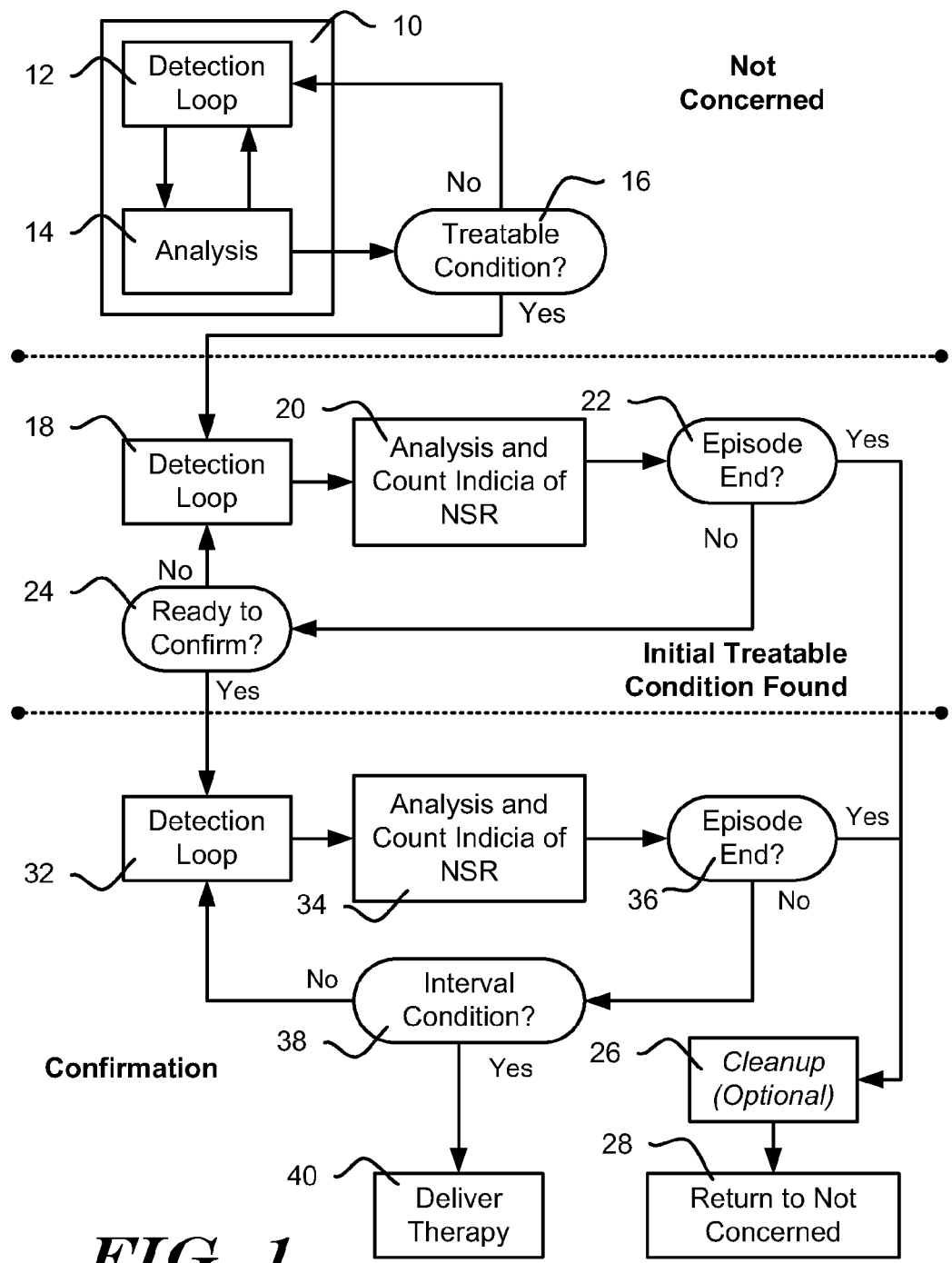
FIG. 1 shows, in block form, an illustrative method for managing detection results during and after charging in an ICSD.

FIG. 1 shows, in block form, an illustrative method for managing detection, analysis and therapy delivery in an ICSD. Three general states of operation are shown—at the top, a Not Concerned state, in the middle, a Initial Treatable Condition Found State, and at the bottom, a Confirmation state. The Not Concerned State implies that a treatable condition, such as a ventricular or atrial arrhythmia has not been identified. The Initial Treatable Condition Found State indicates that a treatable condition has been identified and the ICSD is preparing to delivering therapy. The Confirmation state indicates that the ICSD is performing analysis to confirm that therapy should be delivered.

In one example, an ICSD may be designed to wait for a period of time or a number of cardiac events or detected events before delivering therapy after it identifies a treatable condition. In yet another example, an ICSD may be designed to make a first, initial identification of treatable condition, but waits for a reconfirmation of the treatable condition after clearing out data used in the initial identification. For example, an ICSD may include a capacitor and a charging circuit, and the Initial Treatable Condition Found state can be used while the ICSD charges the capacitor to a desired therapy voltage. When the desired therapy voltage is reached, analysis confirms therapy should be delivered in the Confirmation state. Once therapy is confirmed, the ICSD may adjust the charge on the capacitor to ensure the correct output energy and delivers therapy. Capacitor charging and other conditions may each be applied in parallel by requiring, for example, that the ICSD wait at least a predefined period of time, as well as that the ICSD wait until a capacitor is charged to a desired level and, once both conditions are met, the device is ready to deliver therapy and can advance to the Confirmation state.

The Not Concerned State shows detection loop 12, which applies criteria designed to detect cardiac events. One example compares a detection profile to sensed signal amplitude, using methods known in the art. Once an event is detected, analysis 14 is called to determine whether a detected event or series of detected events indicate a treatable condition, such as an arrhythmia. The specific method of detecting a treatable condition may vary. In one example, the analysis 14 uses event rate as a first indicator of whether a treatable condition is occurring. For example, if the calculated event rate is high, a treatable tachyarrhythmia may be occurring. Morphology may be considered including, for example, considerations such as correlation to a template, QRS width, beat-to-beat stability, or other factors. Interval or rate variability may be monitored, and/or sudden onset or acceleration may be analyzed. In some examples, analysis 14 may determine that a detected event occurred due to noise or overdetection and, if so, the system may return to detection loop 12.

The method continues to block 16 and determines an initial identification of a treatable condition should be made. Block 16 may include further analysis of an overall rhythm or cardiac state. In one example, block 16 reviews the adjudication by analysis block 14 of a number of detected events, for example, 8, 12, 16, 24, 32, 40 or more or some other number of events. An X/Y filter would then be generated by looking, for example, for 18/24 detected events to demonstrate a particular characteristic such as high rate, a particular morphology, a mismatch to a morphology template, large width, high variability, or some mix thereof. In another example, an asynchronous block of time may be analyzed at block 16.

If the outcome of Treatable Condition block 16 is No, the method returns to the detection loop 12. If the outcome of the Treatable Condition block 16 is Yes, the method continues to the Initial Treatable Condition Found state.

The Initial Treatable Condition Found State allows the device to prepare for therapy delivery. At this point an episode can be declared by the ICSD. The term "episode" indicates a particular state of the ICSD that can be called in response to identification of a condition that can be closely analyzed and, if desired, recorded for later download by a physician, such as a potential/likely arrhythmia. During an episode, the ICSD may prepare to deliver therapy, deliver therapy, perform additional data analysis, record and store sensed/detected signals for later retrieval, and/or generate a warning (vibration or emitted sound, for example) to indicate therapy may be imminent. In addition, an Episode may cause the ICSD to attempt communications with an external device such as a bedside monitor or hospital information network or any other external system adapted to receive ICSD communication such as a cellular telephone network, WI-FI, Bluetooth, etc.

Episodes typically end when the identified condition ends, for example, following spontaneous reversion to a benign rhythm or return to benign rhythm after therapy delivery. If therapy is delivered and fails, some systems will repeat therapy delivery until the arrhythmia is terminated or a maximum number of therapy attempts have been performed. A system may also progress through a number of different therapies, for example applying ATP in one or more formats and then moving on to cardioversion or defibrillation if the arrhythmia is not terminated. Where multiple therapies (repeating the same therapy or applying different therapies) are delivered, the methods shown herein may be repeated for each therapy delivery sequence. Alternatively, in another embodiment, the confirmation processes may be performed for only the first therapy delivery of an episode.

In the Initial Treatable Condition Found state, the method again uses a detection loop 18 to determine whether an event has been detected. Detection loop 18 and detection loop 12 may apply similar or different criteria to identify detected events, depending upon the embodiment and/or physician preferences. Once a detected event occurs, the method goes to block 20, which performs analysis and initiates a count of indications of benign cardiac conditions.

The analysis in block 20 can be performed, in an illustrative example, by counting how many indications of benign cardiac conditions appear during the episode. The analysis from block 20 can be used to delay therapy delivery if numerous indications of benign cardiac condition have appeared and, conversely, if no such benign indications have appeared, the analysis in block 20 will allow therapy to be delivered once ready. The analysis in block 20 can observe various types of markers of benign cardiac activity including, in some examples, slow rate detections.

In addition, the analysis in block 20 may also track the time series of events that indicate either benign or treatable conditions. For example, confirmation criteria may be changed in response to detected events suggesting a benign condition. If subsequent events suggest a treatable condition has returned, the confirmation threshold may be returned to its original state.

Following analysis at 20, the method determines whether the episode has ended, as shown at 22. In an illustrative example, the episode is considered ended if a calculated rate is below a set threshold for a predetermined number of events, calculations or period of time. For example, if the calculated rate is below 140 beats per minute (BPM) for 24 consecutive detections, the episode is considered terminated. In another example, if the average calculated rate for a set of 25 calculations is less than 120 BPM, the episode is considered terminated. In yet another example, if the rate is less than 100 BPM in 20/25 previous calculations, the episode is considered terminated. Other criteria may be used in other embodiments in order to determine that the episode has ended. If the episode has ended at 22, the method proceeds to a cleanup block 26.

The cleanup block 26 may include steps for discharging the defibrillation capacitor (if it was charged in the Initial Treatable Condition Found State) and storing data for the terminated episode. Cleanup 26 may include other steps including, for example, annunciation or attempts to initiate communication with a home monitoring system. Following cleanup 26, the method returns to the Not Concerned state as indicated at 28. If desired, cleanup 26 may include changes to the analysis of the Treatable Condition block 16 in response to a nonsustained episode. Some examples are disclosed in US Patent Application Publication Numbers 2009-0131998 and 2006-0167503, both titled METHOD FOR ADAPTING CHARGE INITIATION FOR AN IMPLANTABLE CARDIOVERTER-DEFIBRILLATOR, as well as US Patent Application Publication Number 2006-0167504, titled DEVICES FOR ADAPTING CHARGE INITIATION FOR AN IMPLANTABLE CARDIO-VERTER-DEFIBRILLATOR, the disclosures of which are incorporated herein by reference. In one illustrative example, a persistence factor used in the Treatable Condition block 16 is modified in response to an episode ending without therapy delivery. For example, an X/Y counter may be used to determine how many Treatable detections (X) out of a set of Y detections have been encountered. When the X/Y counter reaches a predetermined threshold and stays at or above the threshold for a persistence number (N) of consecutive events, the charge begin block 16 is satisfied. Following termination of an episode without therapy delivery, the persistence number (N) may be increased for use in a future episode. Other factors, such as the size of the X/Y set and/or the X/Y ratio may be changed, instead.

If the episode has not ended at block 22, the method determines whether the system is ready for therapy delivery, as shown at 24. If so, the method continues to the Confirmation state. If not, the method returns to the detection loop 18. The check at 24 may include, for example, determining how many detected events have occurred while in the Initial Treatable Condition Found state, how long the Initial Treatable Condition Found state has been ongoing, and/or whether any therapy capacitor charging is complete.

In the Confirmation state, analysis again starts in a Detection Loop 32. Following a detection at 32, the method analyzes the detected event and sensed signal to count indications of benign rhythm (denoted in the example as indications of Normal Sinus Rhythm, NSR), as shown at 34. The method next determines whether the episode has ended, as shown at 36. Finally, an Interval condition is applied as shown at 38. The Interval condition determines whether the intervals between detected events are shorter than a short interval threshold for at least a threshold number of intervals. In an illustrative example, the short interval threshold is an arrhythmia rate threshold that can be set via programmer communications to a value corresponding to a rate of 140 to 270 BPM. The threshold number of intervals is determined by adding up the number of indications of NSR that were counted in blocks 20 and 34, plus a default minimum number. If benign conditions are detected, therapy delivery can be delayed until additional indications of treatable conditions are identified. If desired, the sum of indications of NSR from blocks 20 and 34 may be discounted in response to indications of VF or VT when applying the condition at 38.

If the Interval condition fails at 38, the method returns to the detection loop at 32, staying in the Confirmation state. If the Interval condition 38 is met, therapy is delivered, as indicated at 40. If therapy is delivered at 40, the method will continue within the same episode, using a post-therapy state (not shown) including detection and analysis to determine whether to start additional therapy cycles, as well as analysis to determine whether therapy has been successful and the episode has ended.

Figure 2:
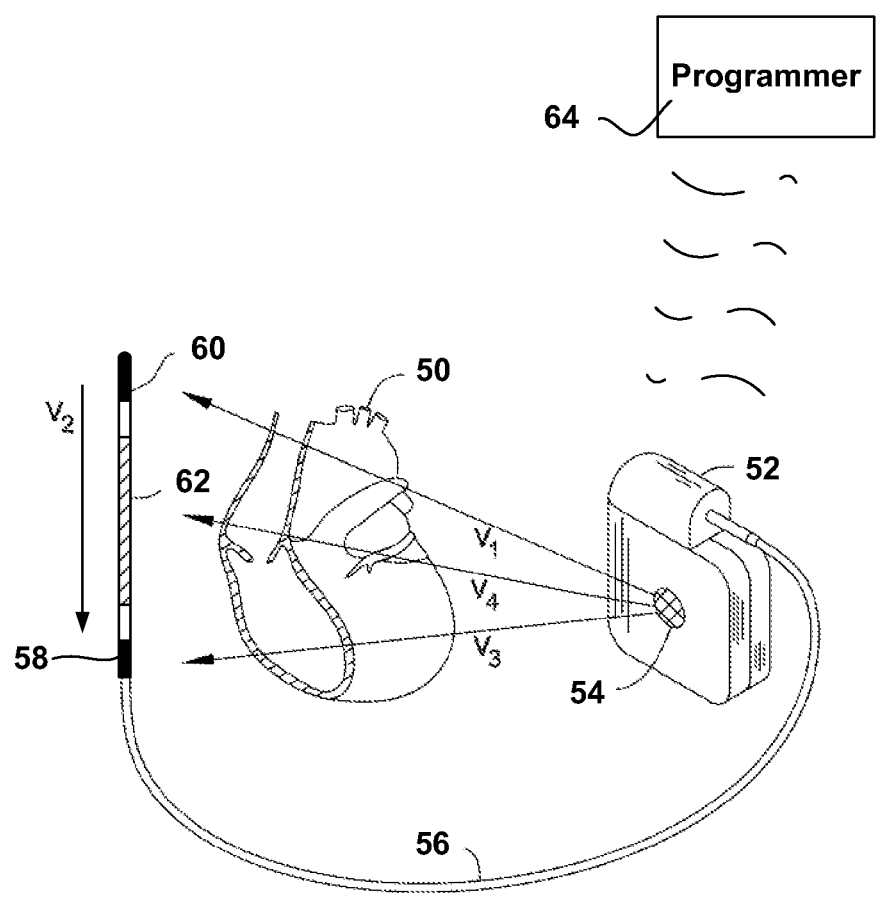
FIG. 2 shows an illustrative implantable cardiac stimulus system relative to a patient's heart.

FIG. 2 shows an illustrative implantable medical device and implant location. More particularly, an illustrative subcutaneous-only ICSD system is shown in FIG. 2. The system is shown relative to a heart 50, and includes a canister 52 coupled to a lead 56. The canister 52 preferably houses operational circuitry for performing analysis of cardiac activity and for providing a therapy output. The operational circuitry may include batteries, input/output circuitry, power capacitor(s), high voltage charging circuit(s), logic circuits, controller(s), memory, communication components, etc., as known in the art.

Electrodes are disposed at locations throughout the system including, for example, an electrode 54 on the canister 52, and electrodes 58, 60, 62 on lead 56. The electrodes 54, 58, 60, 62 may take any suitable form and can be made of any suitable material. For example, the canister electrode 54 may be an isolated button electrode or it may be a region or surface of the canister 52, and the electrodes 58, 60, 62 on lead 56 may be coil electrodes, ring electrodes, or other structures known in the art. More or fewer electrodes may be provided on the canister 52 and or the lead 56.

The electrodes 54, 58, 60, 62 define a plurality of sensing vectors such as V1, V2, V3 and V4. If desired, one or more vectors V1, V2, V3, and V4 may be chosen as a default sensing vector, for example, as discussed in US Patent Application Publication Number 2007-0276445 titled SYSTEMS AND METHODS FOR SENSING VECTOR SELECTION IN AN IMPLANTABLE MEDICAL DEVICE and/or U.S. Pat. No. 7,392,085 titled MULTIPLE ELECTRODE VECTORS FOR IMPLANTABLE CARDIAC TREATMENT DEVICES, the disclosures of which are incorporated herein by reference. Another embodiment considers posture in vector analysis, for example, as discussed in US Patent Application Publication Number 2008-0188901 titled SENSING VECTOR SELECTION IN A CARDIAC STIMULUS DEVICE WITH POSTURAL ASSESSMENT, the disclosure of which is incorporated herein by reference. Multiple sensing vectors may be analyzed, sequentially or in combination, as desired.

Therapy may be applied using any chosen pair of electrodes. An illustrative example uses the can electrode 54 and the coil electrode 62 to apply therapy. Other electrode combinations may be used. Therapy may include mono-, bi- or other multi-phasic defibrillation and/or various pacing operations.

FIG. 2 omits several anatomical landmarks. The illustrative system shown may be implanted beneath the skin outside of the ribcage of the implantee. The location illustratively shown would place the canister 52 at approximately the left axilla of the implantee, level with the cardiac apex, with the lead 56 extending medially toward the xiphoid and then toward the head of the implantee along the left side of the sternum. One illustrative example uses a method/system as shown in commonly assigned US Patent Application Publication Number 2006-0122676 entitled APPARATUS AND METHOD FOR SUBCUTANEOUS ELECTRODE INSERTION, the disclosure of which is incorporated herein by reference. Other illustrative subcutaneous systems and locations are shown in commonly assigned U.S. Pat. Nos. 6,647,292, 6,721,597 and 7,149,575, the disclosures of which are incorporated herein by reference.

The present invention may also be embodied in systems having various implant configurations including but not limited to other subcutaneous-only, vascular-only, epicardial, and/or transvenous implantation configurations and locations. The canister 52 may be placed in anterior, lateral, and/or posterior positions including, without limitation, axillary, sub-clavicular, pectoral, and sub-pectoral positions, as well as placements on either the left or right side of the implantee's torso and/or in the abdomen. The canister may be a single unit or it may comprise a number of connected or tethered enclosures in various designs known throughout the art. Entirely intravascular implantation of an ICSD system has also been proposed. The lead 56 may be placed in any of a number of suitable configurations including anterior-posterior combinations, anterior-only combinations, transvenous placement, or other vascular placements. Multiple leads 56 may be used as well. A unitary system that omits lead 56 and includes all electrodes on the canister 52 may also be used.

The present invention is not intended to be limited to any particular hardware, implant location or configuration. Instead, it is intended for use in any implantable cardiac system. In addition to therapy delivery systems, some embodiments may include monitoring systems. For example, monitoring functions such as annunciation or data storage may be manipulated, rather than controlling therapy delivery. A monitoring system could also be used to demonstrate the suitability of analytical methods for a particular patient.

Some examples can associate with an external programmer 64 configured to communicate with an implanted device for various purposes, including, for example and without limitation, one or more of the following: device testing; upload new/revised software/firmware; modify sensing, detection or therapy settings; determine the status or history of device operation, battery life, or lead integrity; and/or download data relating to the device or implantee's condition, prior data capture, or treatment. Any suitable communication method may be used, such as various protocols and hardware widely known in the art including, for example, MICS, inductive telemetry, RF telemetry, Bluetooth, etc.

Figure 3:
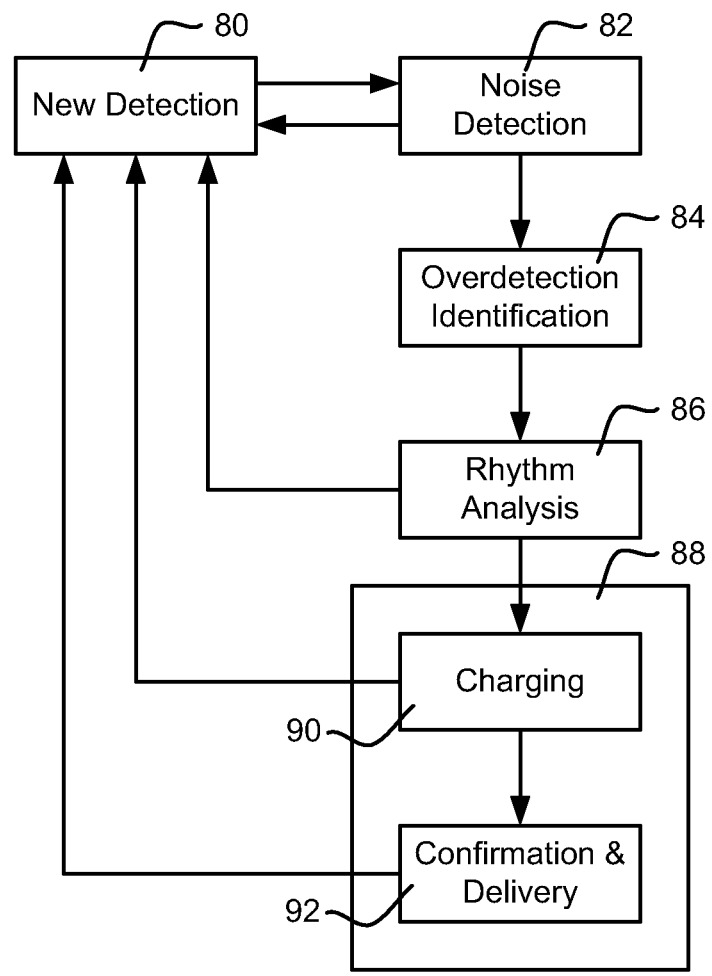
FIG. 3 shows, in block form, an illustrative method of operating an ICSD.

FIG. 3 shows, in block form, an illustrative method of operating an ICSD for purposes of delivering relatively high-energy therapy such as defibrillation or cardioversion. In the illustrative method, a new detection 80 is the trigger for a series of analysis steps. A new detection 80 may be identified, for example, by capturing a cardiac signal from implanted electrodes associated with the system and comparing the sensed signal to a detection threshold. A detection threshold may be fixed or it may be a time-varying threshold, for example as shown in US Patent Application Publication Number 2009-0228057, titled ACCURATE CARDIAC EVENT DETECTION IN AN IMPLANTABLE CARDIAC STIMULUS DEVICE, the disclosure of which is incorporated herein by reference. Other detection methods may be used instead.

In the illustrative example, following a new detection 80, Noise Detection is performed as shown at 82. Noise Detection 82 may be performed to identify detections that appear to be caused by noise or substantially masked with noise. If a detection appears to be caused by noise or substantially masked with noise, the method can return to block 80 and await the next detection.

Otherwise, Overdetection Identification 84 is performed. Overdetection Identification may take any of several forms. Overdetection identification 84 is included to identify (and correct, if suitable) instances where more than one detection occurs within a single cardiac cycle such as double or triple detection.

Rhythm Analysis 86 follows, in which the patient's overall cardiac rhythm is analyzed to determine whether a treatable arrhythmias. Rate will often be a factor in Rhythm Analysis 86. In some examples, rate may be analyzed before blocks 84 or 86 and, if the calculated rate is low, the method may return to block 80. Morphology, width, and other factors may be part of Rhythm Analysis 86.

If the Rhythm Analysis 86 finds that the patient's cardiac rhythm is benign and does not require treatment, the method returns to block 80 and awaits the next detection. If Rhythm Analysis 86 identifies a treatable arrhythmia, Therapy block 88 is called. Therapy block 88 may include charging 90 for the cardioversion/defibrillation capacitor in the ICSD. If charging 90 is not complete, the method returns to block 80 for a next iteration.

Once charging 90 is complete, Therapy block 88 confirms ongoing need for therapy and, if therapy is confirmed, therapy is delivered at 92. If confirmation fails, the method again returns to block 80 for a next iteration. In another example, ATP can be provided, in which case the charging block 90 can be omitted or replaced with another analysis block that observes whether the device is ready to deliver therapy. Whether the device is ready to deliver therapy may be determined by, for example, meeting confirmation criteria, observing that the treatable condition has not terminated in a predetermined period of time, or determining that an arrhythmia is progressing to a worse state than was initially detected.

The Noise Detection referenced at block 82 of FIG. 3 may include waveform appraisal as described in commonly assigned U.S. Pat. No. 7,248,921, titled METHOD AND DEVICES FOR PERFORMING CARDIAC WAVEFORM APPRAISAL, and/or U.S. Provisional Patent Application No. 61/255,253, titled ADAPTIVE WAVEFORM APPRAISAL IN AN IMPLANTABLE CARDIAC SYSTEM, the disclosures of which are incorporated herein by reference. Overdetection identification 84 may be performed, for example, using methods such as shown in US Patent Application Publication Number 2009-0259271, titled METHODS AND DEVICES FOR ACCURATELY CLASSIFYING CARDIAC ACTIVITY, and/or US Patent Application Publication Number 2010-0004713, titled METHODS AND DEVICES FOR ACCURATELY CLASSIFYING CARDIAC ACTIVITY, the disclosures of which are incorporated herein by reference. Rhythm analysis 86 may include analysis as disclosed in the 2009-0228057, 2009-0259271 or 2010-0004713 Application Publications, the U.S. Pat. No. 7,248,921 and/or commonly assigned U.S. Pat. No. 7,330,757 or U.S. Pat. No. 6,754,528, the disclosures of which are incorporated herein by reference. Other methods may be used instead of or in addition to any of the examples found in these patents and patent applications.

Figure 4:
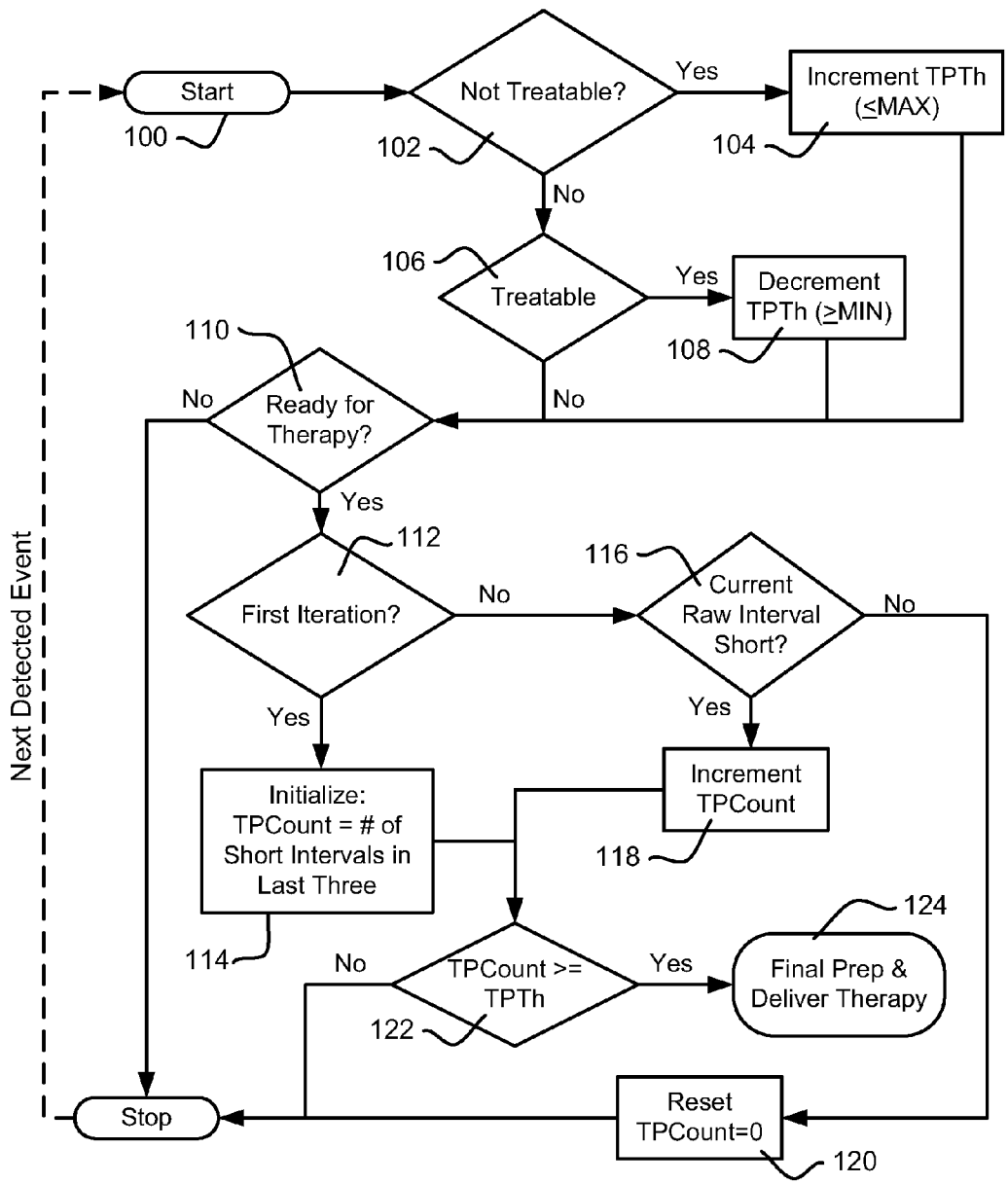
FIG. 4 is a process flow diagram for an illustrative method for managing therapy delivery.

FIG. 4 is a process flow diagram for an illustrative method for adapting the conditions for therapy delivery to a detected rhythm. The management of therapy delivery in FIG. 4 accounts for indications of benign cardiac activity before delivery of therapy. As a result, therapy delivery may be avoided in response to relatively late reversion to a benign cardiac rhythm. Before explaining the solution posed by the method illustrated in FIG. 4, FIG. 5 shows an example of therapy delivery that could be avoided by counting indications of benign cardiac activity.

Figure 5:
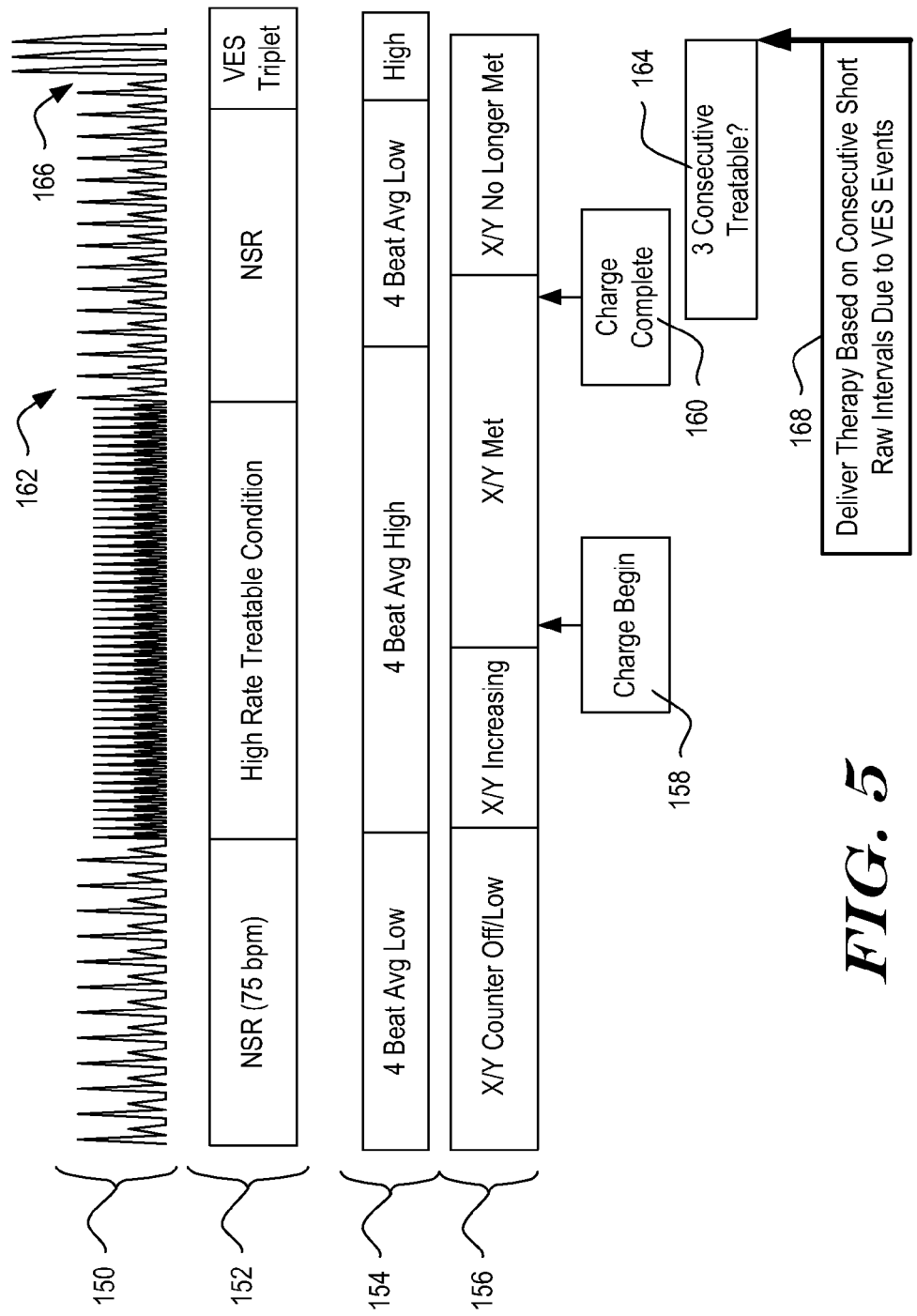
FIG. 5 is an illustration of analysis using a "Last 3 intervals" therapy confirmation criteria.

Turning to FIG. 5, a sensed signal is shown at 150. The signal 150 is characterized at 152. The illustrative system relies on an average of calculated intervals between detected events to generate an Event Rate, which is characterized at 154. In the example an X/Y counter is used to determine how many treatable events (X) out of a set of detected events (Y) occur. The contents of the X/Y counter are characterized at 156. Starting from the left, the patient is in a normal rhythm. A high rate arrhythmia begins that, as indicated at 154, drives the Event Rate high (relative to a programmed rate threshold), and, as indicated at 156, the X/Y counter begins to fill with treatable events.

When the X/Y counter meets certain analysis threshold(s), charging begins, as shown at 158. Before charging is completed 160, the arrhythmia spontaneously reverts and slows down to a normal sinus rhythm, as shown at 162. This drops the Event Rate to a low zone. Therapy delivery after the high rate arrhythmia terminates is likely not needed. However, during the normal sinus rhythm 162, the patient encounters a short series of detected events caused by ventricular extrasystoles (VES), shown at 164. A premature ventricular contraction is one type of VES.

In the illustrative example, the confirmation criteria include the following: if three consecutive intervals are shorter than a predetermined threshold, therapy is delivered. Here, the VES cause a series of very short intervals between detected events. Once three short intervals occur, therapy is delivered, as shown at 168. The therapy in these circumstances is likely clinically unnecessary and may be painful and/or startling to the patient.

The method of FIG. 4 may avoid therapy as shown in FIG. 5. The method illustrated by FIG. 4 may be used at blocks 90 and/or 92 in FIG. 3, for example. The method begins at the start block 100; the conditions precedent to start block 100 are the occurrence of a newly detected event, and, optionally, initial identification of a treatable cardiac condition.

From start block 100, the method determines whether a detected event under analysis has been identified as non-Treatable, as indicated at 102. If so, then a Therapy Persist Threshold, TPTh, is incremented. Optionally, a maximum value for TPTh may be set, for example, a maximum may be in the range of about 8-64, with larger or smaller values possible depending upon how the variable is used. In one example, the maximum value for TPTh is 24.

Returning to block 102, if the event under analysis has not been marked as non-Treatable, the method next determines if the event under analysis has been marked as Treatable, as shown at 106. If so, then TPTh is decremented, as shown at 108. If desired, TPTh may have a lower limit, as shown in FIG. 4. In an illustrative example, TPTh has a lower limit of three.

In the example of FIG. 4, if the event under consideration is marked as Noise, for example based on Noise Detection (FIG. 3 at 82), it may pass through without incrementing 104 or decrementing 108. Following the analysis of Treatable/nonTreatable 102, 106 and increment/decrement steps 104, 108, if needed, the method continues to block 110.

At block 110, the method determines whether the ICSD is ready for therapy. Block 110 may, for example, determine that a minimum period of time has passed since the initial identification of a treatable condition, and/or it may include determining that capacitor charging is complete, indicating that the ICSD defibrillation capacitor(s) has been charged to a desired voltage/energy level. If the ICSD is not ready for therapy delivery, the method stops as indicated, and waits for another new detection.

If the conditions of block 110 are satisfied, the method next determines whether it is following a first iteration, as shown at 112, after declaring ready for therapy at block 110. If so, a variable, Treatment Persist Count (TPCount), is initialized to the number of Treatable intervals that have occurred in the last three detected intervals, as indicated at 114. If not in the first iteration, the method continues by observing whether the most recent detected interval is shorter than a threshold for short intervals, as shown at 116. If so, TPCount is incremented by one, as shown at 118 and, if not, TPCount is reset to zero, as shown at 120. In this example, when a string of short intervals is identified, TPCount will increase with each new short interval as shown at 118, while a long interval will cause TPCount to reset to zero as shown at 120. If TPCount is reset at 120, then the method stops, as shown, and waits for a next iteration caused by a next detected event.

In the example of FIG. 4, a "short" interval is an interval that is shorter than a defined threshold that is indicative of a likely treatable arrhythmia. In some examples, the defined threshold for short intervals will be set based on a ventricular tachycardia (VT) rate, for example, if a physician determines that rates above 200 BPM would be treatable tachycardia for a particular patient, the defined VT threshold would be 300 milliseconds. A shorter or longer interval may be used, depending on patient characteristics. If desired, a fibrillation-based threshold may be used. For example, ventricular fibrillation (VF) may be declared for rates above a threshold such as 240 BPM, and a short interval may be an interval shorter than 250 milliseconds. The system may be customized for a given patient by adjusting these thresholds. Other "short" intervals unrelated to VT or VF thresholds may be used instead, and the calculation of TPCount does not need to be tied to defined therapy or rhythm classification thresholds.

Following Initialization at 114 or an increment at 118, the method continues to 122, where TPCount is compared to TPTh. If TPCount is greater than or equal to TPTh, the method then performs final therapy preparations (if needed) and delivers therapy to the patient as shown at 124. Alternatively, if TPCount is not greater than or equal to TPTh, the method stops and awaits the next detection.

As can be seen, the method in FIG. 4 will count long intervals and use these as indications of non-treatable cardiac rhythm to extend TPTh. As a result, if indications of benign cardiac rhythm are identified, the method causes the system to wait to deliver therapy for some number of additional treatable detections. This may avoid therapy delivery if a patient experiences spontaneous reversion to benign cardiac rhythm and/or receives successful external defibrillation therapy. Meanwhile, if the system detects few or no nontreatable or long interval events, TPTh remains small, and the patient will receive therapy shortly after the ICSD meets readiness conditions at 110.

Any number of features may be used to identify benign cardiac conditions. In one example, comparison to a normal beat template may be used to identify indications of benign cardiac rhythm. A normal beat template may be a template captured at a resting heart rate as representative of Normal Sinus Rhythm, and/or a normal beat template may represent a heart beat at elevated rate conditions such as exercise induced tachycardia. High correlation to a normal beat template may be an indication of benign cardiac conditions, even with concurrent high detected cardiac rate.

The confirmation concept can be used to confirm therapy delivery of any sort including ATP, cardioversion or defibrillation. Furthermore, these illustrative examples may be used in treatment of ventricular or atrial conditions. For example, a confirmation step may be applied before delivering therapy for polymorphic ventricular tachycardia, ventricular fibrillation, atrial fibrillation or flutter, for example. Depending upon patient needs, other conditions may also be treated.

The present invention is not limited to any particular method of identifying indicators of treatable or non-treatable cardiac conditions. Several examples refer to marking an event as treatable or not treatable, where "event" refers to individual detected events and not the overall episode (for example, an episode may include a period of ventricular fibrillation including a number of treatable detected events). In some examples, rather than marking "events" as treatable, the intervals associated with detected events can be marked as treatable or not treatable. For example, rate-only analysis may mark intervals between detections as treatable or not treatable; a morphology-only analysis may mark the individual detections as treatable or not treatable. In a hybrid of these analyses, an interval between detected events is associated with either the detected event that precedes the interval or the detected event that ends the interval, and the morphology of the event and the duration of the interval may each factor into marking the associated pair of detected event and interval as treatable or not treatable. In yet another example, the morphology of the signal during an interval between detected events can be analyzed to identify treatable conditions as well.

In some examples, the confirmatory criteria may add additional data inputs to the analysis by, for example, making reference to accelerator data (indicating activity or posture), blood pressure sensors, blood composition sensors or other data. Such additional data inputs can be used in combination with the above described confirmatory criteria.

Figure 6A:
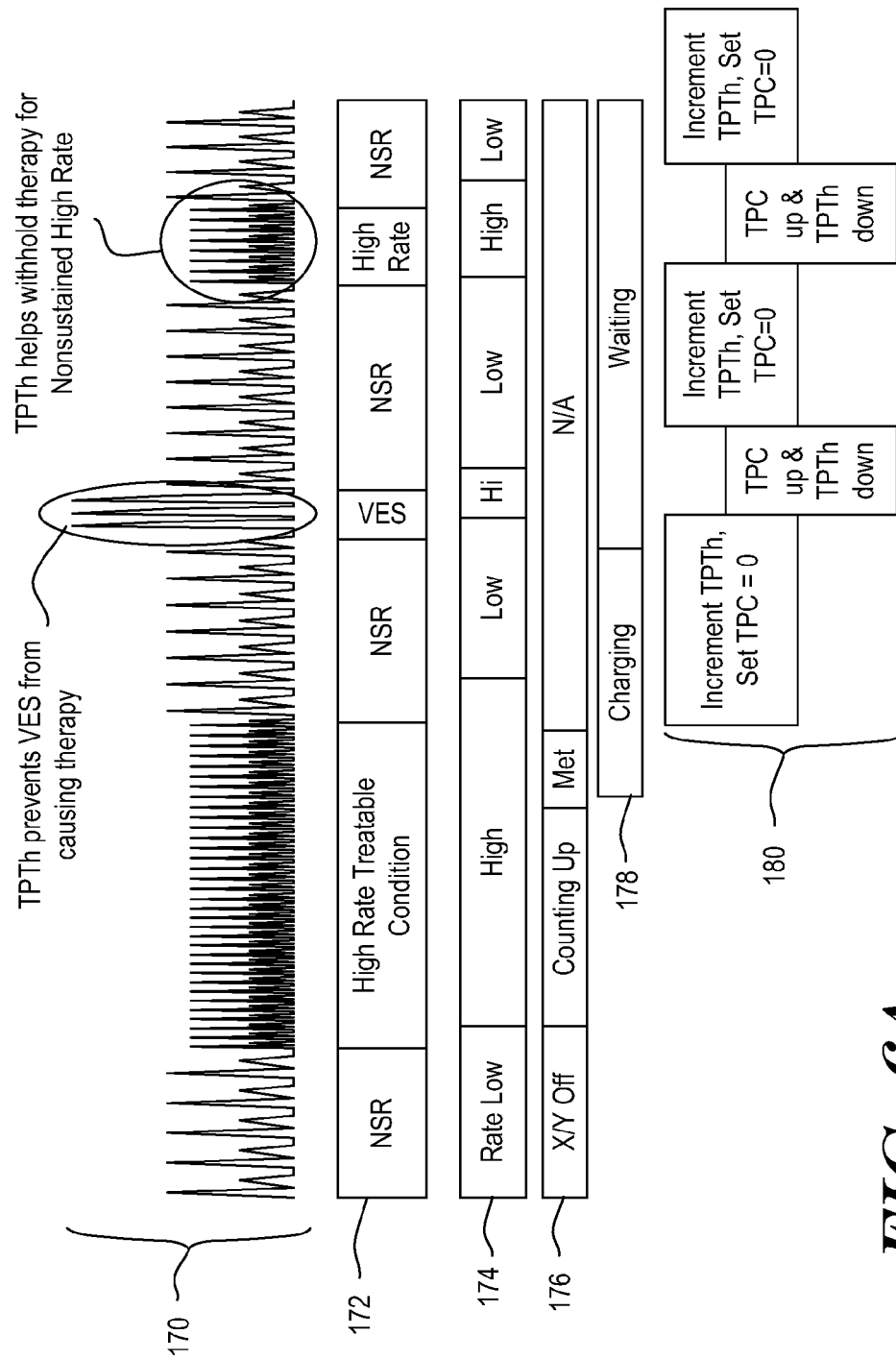
FIGS. 6A-6C illustrate analysis similar to FIG. 5, except with different therapy confirmation criteria applied.
Figure 6B:
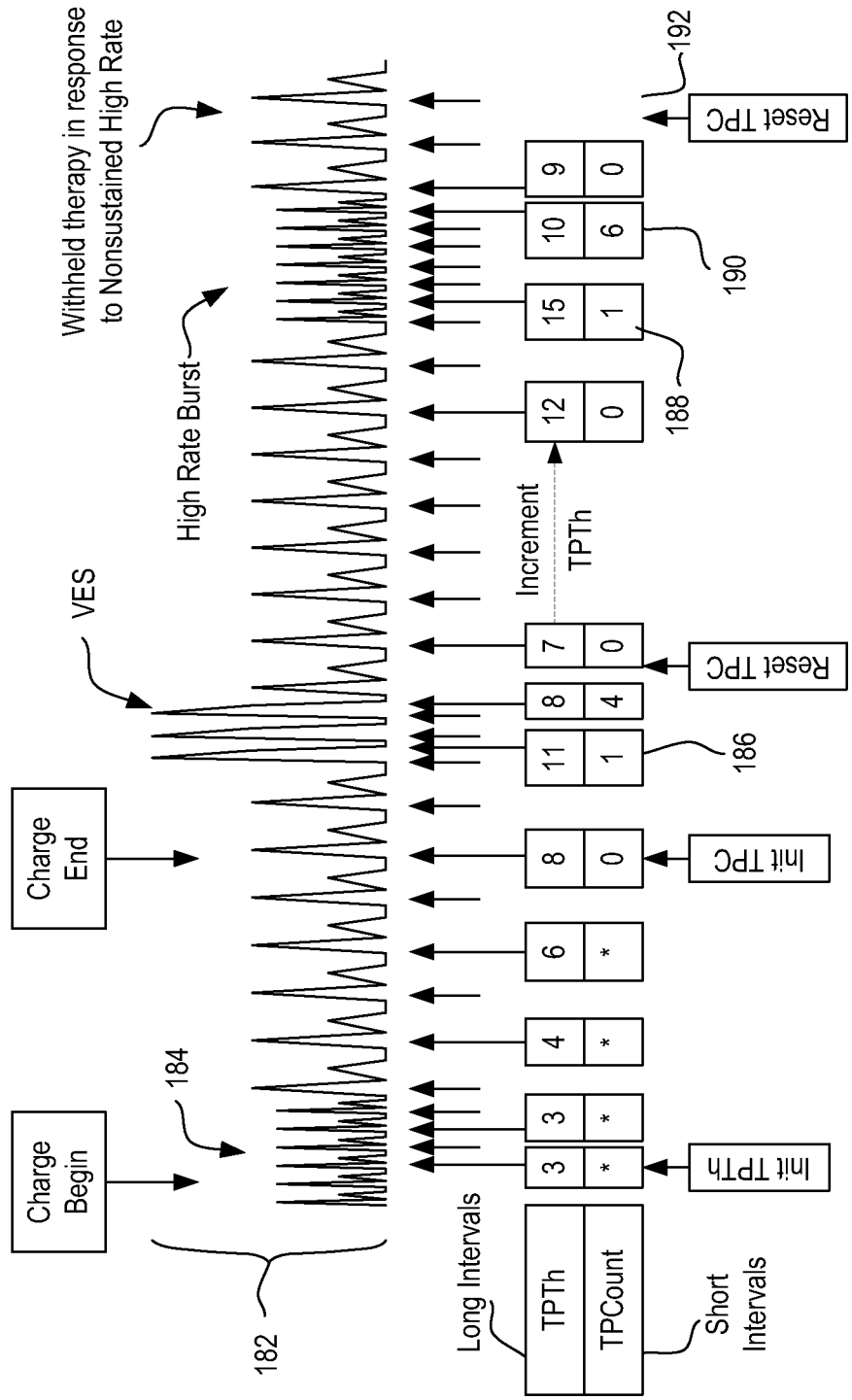

FIGS. 6A-6B show analysis in a format similar to FIG. 5, but using the methods shown in FIG. 4. Referring to FIG. 6A, the top of the drawing shows sensed cardiac signals at 170. The cardiac signals are characterized at 172. The ICSD analysis of the signal is indicated in part by the Event Rate, characterized at 174, and the status of the X/Y counter shown at 176.

The status of the system's Charger, which is used to charge a therapy capacitor, is shown at 178. The example of FIGS. 6A-6B illustrates a system preparing for a defibrillation or cardioversion therapy; in other examples, rather than charger status, a timer status could be shown as counting how long a treatable condition persists before delivering therapy, for example, if the therapy does not require charging. For example, before delivering ATP the system may wait for a predetermined period of time.

Starting from the left, the signal 170 is initially shown as normal at 172, with low rate 174 and the X/Y counter 176 is low/off. Given the normal rhythm, charging has not started. Following the signal across to the right, the patient then develops a tachycardia, as shown at 170, and characterized at 172, leading to a high rate calculation 174. The X/Y counter 176 begins to count indications of treatable condition based on the high Event Rate. The charger remains off, pending satisfaction of rhythm criteria.

In the example, the X/Y counter is used to apply rhythm criteria by counting the number of detections that indicate a treatable arrhythmia. In this example, the high rate calculation 174 indicates a treatable arrhythmia, and the X/Y counter begins incrementing with each detected event that meets the high rate criteria, until a threshold is met. For example, an X/Y counter threshold may be of the nature of 5/8, 9/12, 12/16, 14/18, 18/24, etc., usually requiring a supermajority (such as 75% or some other proportion) of a set of events to indicate a treatable arrhythmia. A persistence rule may also apply, in which the X/Y counter is called upon to meet a threshold for a specified number of consecutive detections or, alternatively, a period of time. For example, persistence may wait until the X/Y counter meets its threshold for at least 2 consecutive measurements, one full second, or some other suitable measure. The persistence rule may increase in duration if prior nonsustained treatable conditions have occurred.

Once the X/Y counter criteria is met (including any persistence factor), the Charger begins charging, as shown at 178. Once the charger begins charging, the system begins calculating a Therapy Persist Threshold (TPTh) and a Therapy Persist Count (TPC) as shown at 180. TPC represents the number of consecutive short intervals currently detected. In this example, TPC counts up as new short intervals are detected, and is reset to zero when a long interval occurs. TPTh records the threshold number that TPC must meet or exceed in order to satisfy Therapy Persist criteria. TPTh varies in response to detected indications of benign and treatable conditions.

In the example, the signal returns to a slow rate (NSR) shortly after charging begins, causing long intervals and lowering the rate calculation 174. As shown at 180, the TPTh monitor begins to count up the number of long intervals when the NSR starts to occur after charge begin. These long intervals are treated in this example as indications of benign cardiac rhythm. TPC is set to zero due to the long intervals. Charging completes as shown at 178 while the NSR is still continuing and the TPTh is still counting up, so the Charger enters a Wait state. The Charger will remain in a Wait state until a Confirmation rule (TPC.gtoreq.TPTh) is satisfied and therapy is delivered, or until the episode ends based on the system's determination that an arrhythmia is no longer occurring.

In an illustrative example, the episode can be terminated if system detects enough slow rhythm beats to determine that the treatable arrhythmia has reverted to a benign rhythm. For example, a fixed number of consecutive long intervals may be required, the X/Y counter may count down to zero, or rate calculated using average intervals may show a low rate for a predetermined period of time or number of consecutive calculations. In one example, if twenty-four low rate calculations 174 appear in a row, a declared episode is considered terminated. In another example, if the X/Y counter reaches three or lower (or zero, in yet another example), the episode is considered terminated. In another example, if a low rate is detected for a period of time in the range of 10-20 seconds, the episode can be considered terminated.

Returning to FIG. 6A, a short burst of VES occurs and causes the rate 174 to momentarily go High which, in turn, begins allowing the method to start counting down TPTh. TPC also starts counting up, but because TPTh counted up during the NSR after charging began, TPC stays less than TPTh. The outcome is that therapy is not delivered in response to the series of VES.

Later, a short burst of VT occurs, again driving the rate 174 high and causing TPC to begin counting up while TPTh counts down. Once again, the incrementing of TPTh during slow rate beats appropriately prevents therapy delivery. The mathematics of this analysis are further highlighted in FIG. 6B.

FIG. 6B provides further details to the analysis of FIG. 6A, focusing on what happens once Charging begins. A portion of the signal from FIG. 6A is shown at 182, with the end of the high rate rhythm that caused charging to begin shown at 184. The values for variable TPTh and TPC are shown below the signal 182. In particular, when charging begins, TPTh is initialized to 3. As shown, during the continuing high rate conditions demonstrated at 184, TPTh stays constant at 3. Once a slow rate condition begins, TPTh starts to count up.

In some examples, TPC is not calculated during charging. In other examples, TPC may be calculated during charging to allow confirmation of therapy delivery as soon as the charging process is completed, without having to wait for TPC to increment up to the lowest value of TPTh. The illustrative example shown in FIG. 6B does not calculate TPC until charging is complete, as indicated by the asterisks.

Once charging ends, in this example, TPC is initialized to zero. In an alternative example, TPC may be initialized based on a series of previously detected events. The illustrative example is iterative, and TCP and TPTh are recalculated by incrementing or decrementing as new detections occur. As shown at 186, TPTh counts up by several increments before a first VES detection appears. As a result, following the first short interval caused by the VES, TPTh=11 and TPC=1. Each of these values is updated with new detections and, at the end of several short intervals caused by the VES, TPTh=8 and TPC=4.

In this example, a 4-interval average is used to estimate rate for TPTh calculations, while the instantaneous interval is used for TPC. Since TPTh is generated from a 4-Interval average in the detailed example shown, it does not immediately begin counting down once the short intervals from the VES occur, as these are averaged in with prior intervals. The use of a 4-interval average is merely illustrative, and other calculations may be performed to estimate rate instead. TPC and TPTh can be based on the same calculation (as shown) or different calculations in various embodiments. The next interval is long, causing TPC to be reset to zero, while TPTh is decremented to seven since it is based on a 4-Interval average.

Following the VES, TPTh again begins to count up. When the first short interval of the VT is detected, TPTh=15, as shown at 188. As shown at 190, when the VT terminates, TPTh=10 and TPC=6. The next calculation, as shown at 192, shows reset of TPC=0, while TPTh=9, as it continues to decrement for one more iteration since it relies on an averaged interval. As can be seen, due to TPC and TPTh, therapy is appropriately withheld even in the presence of a nonsustained VT and several short intervals at the VES triplet.

In the example shown, TPC counts up while TPTh counts down, effectively halving the delay. Some examples avoid this halving effect, for example, TPTh may increment twice for each long interval, and decrement once for each short interval. In addition, to avoid putting off therapy for an undesirably long period of time, TPTh may be capped, for example, with a maximum value in the range of 8-64, or less or more. In one example, TPTh is capped at 24. Other maximum values for TPTh can be used.

Figure 6C:
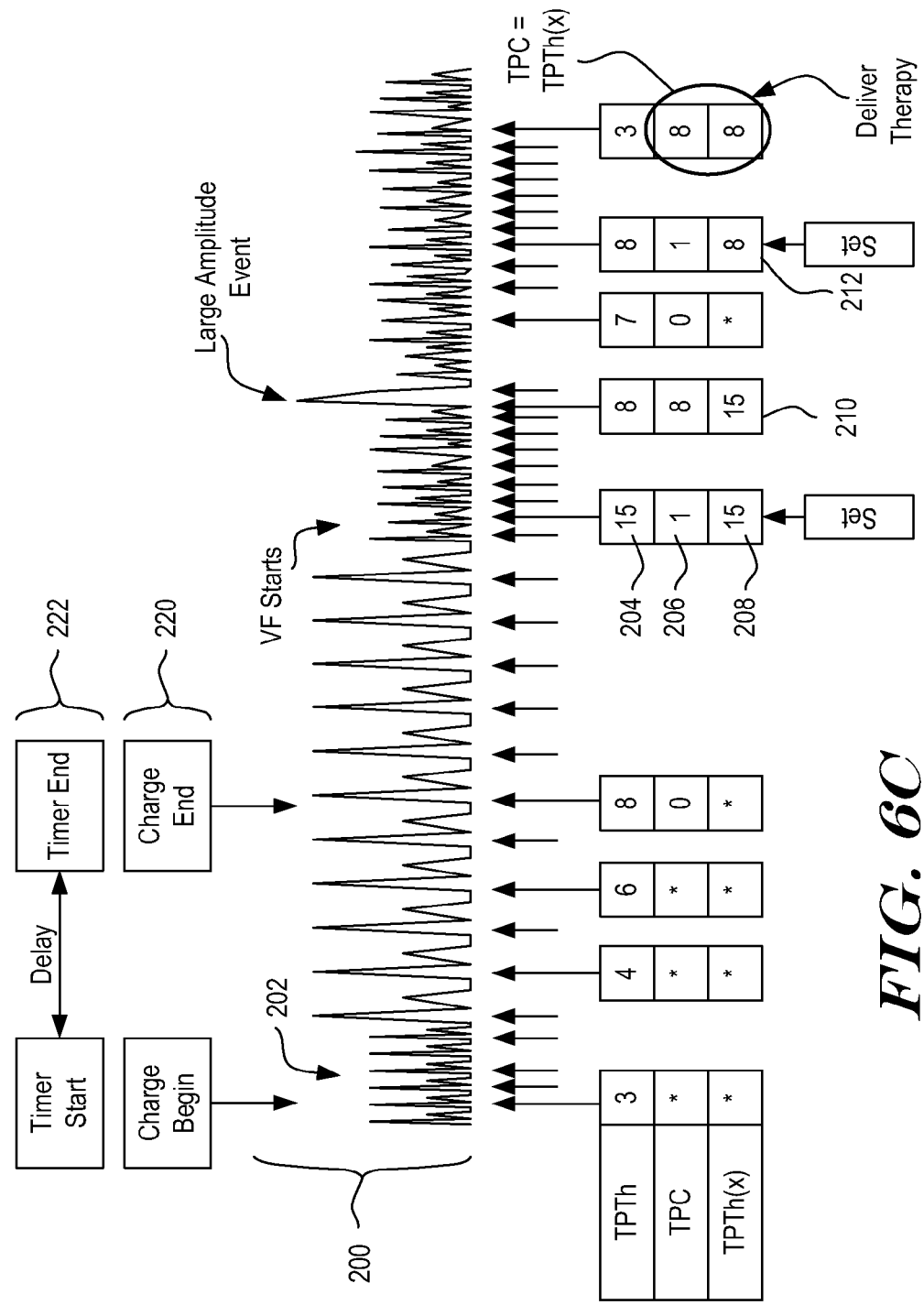

FIG. 6C shows an example that avoids the halving effect caused when TPTh counts down while TPC counts up (shown by FIG. 6B, in particular). A cardiac signal is shown at 200, with a treatable tachycardia represented at 202. The tachycardia 202 causes charging to begin. A new variable, TPTh(x), is used to retain the value of TPTh at the start of a series of short intervals. In the example, during charging the signal 200 reverts to a normal rhythm with long intervals, causing TPTh to count upward. Next, a ventricular fibrillation (VF) starts, as indicated. At the time the VF starts impacting rate, TPTh=15, as shown at 204. When TPC=1, as shown at 206, TPTh(x) is "Set" to equal TPTh, as shown at 208. TPTh(x) retains the "Set" value until the series of short intervals is broken and restarts—that is, until TPC is reset to zero and begins counting up again.

In the example, a large amplitude detection interrupts the detection of VF, leading to undercounting or dropout. As shown at 210, when the large amplitude detection occurs, TPC is still less than TPTh(x). In the example, therapy is inhibited until TPC=TPTh(x), so no therapy is yet delivered. Undercounting following the large amplitude event causes a reset of TPC, and when VF resumes again after the dropout caused by the VES, TPTh(x) is set to the then-current value of TPTh. Therefore, as shown at 212, TPTh(x) is set to equal TPTh, which was at 8 at the time, for use going forward. Because the VF continues, the system proceeds to deliver therapy once TPC=TPTh(x). If the VF were to terminate and return to normal rhythm, for example after the large amplitude event, no therapy would have been delivered in the example.

In another example using ATP and/or where the capacitor charging is not needed or has short duration, a minimum time period may be defined to force a delay period into the system. Thus, rather than showing "Charge Begin" and "Charge End" 220, the method may instead use Timer Start and Timer End 222. The delay may be in the range of 3-10 seconds, or more or less.

Figure 7A:
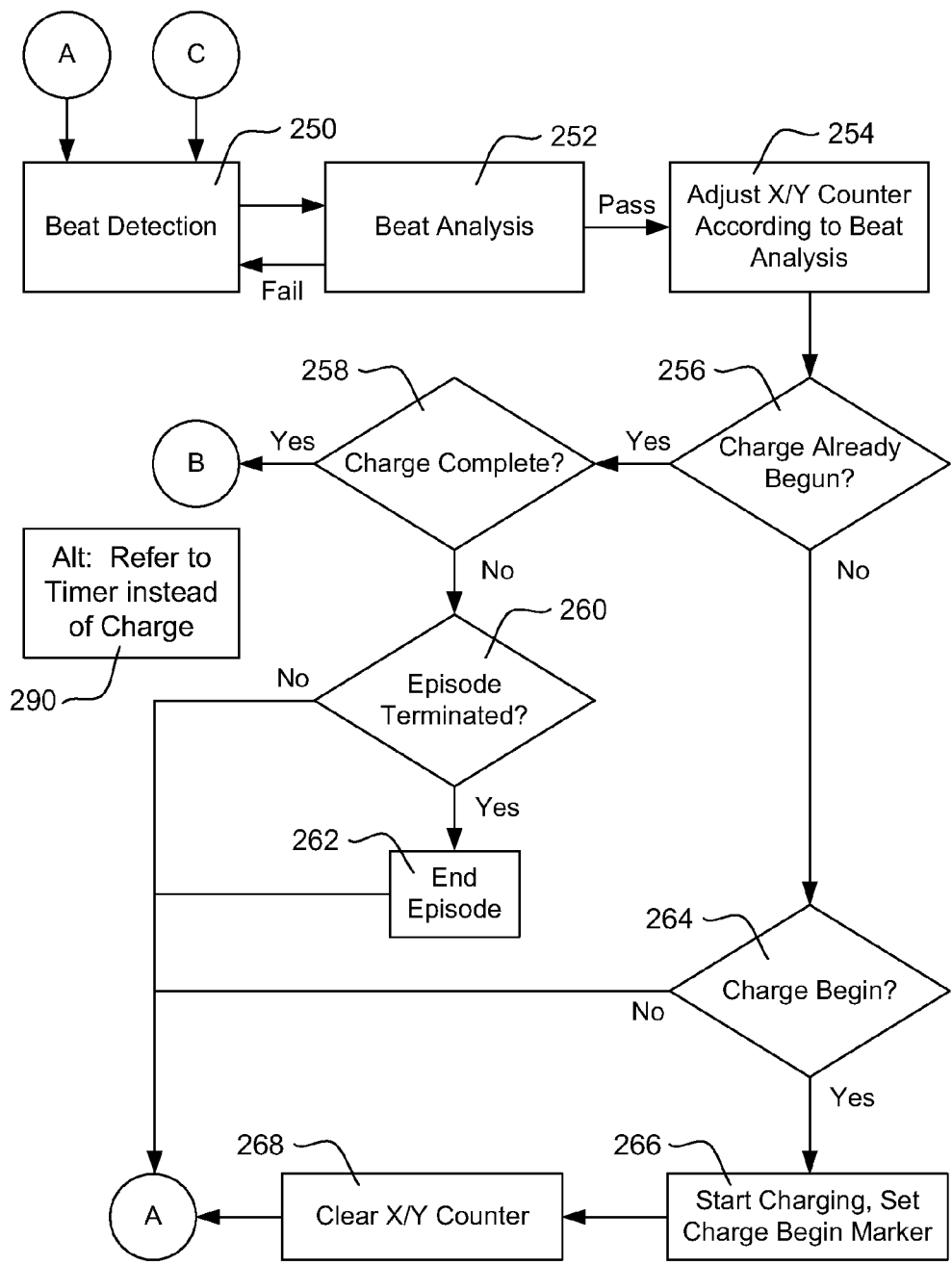
FIGS. 7A-7B show a process flow for another illustrative method for managing therapy delivery.
Figure 7B:
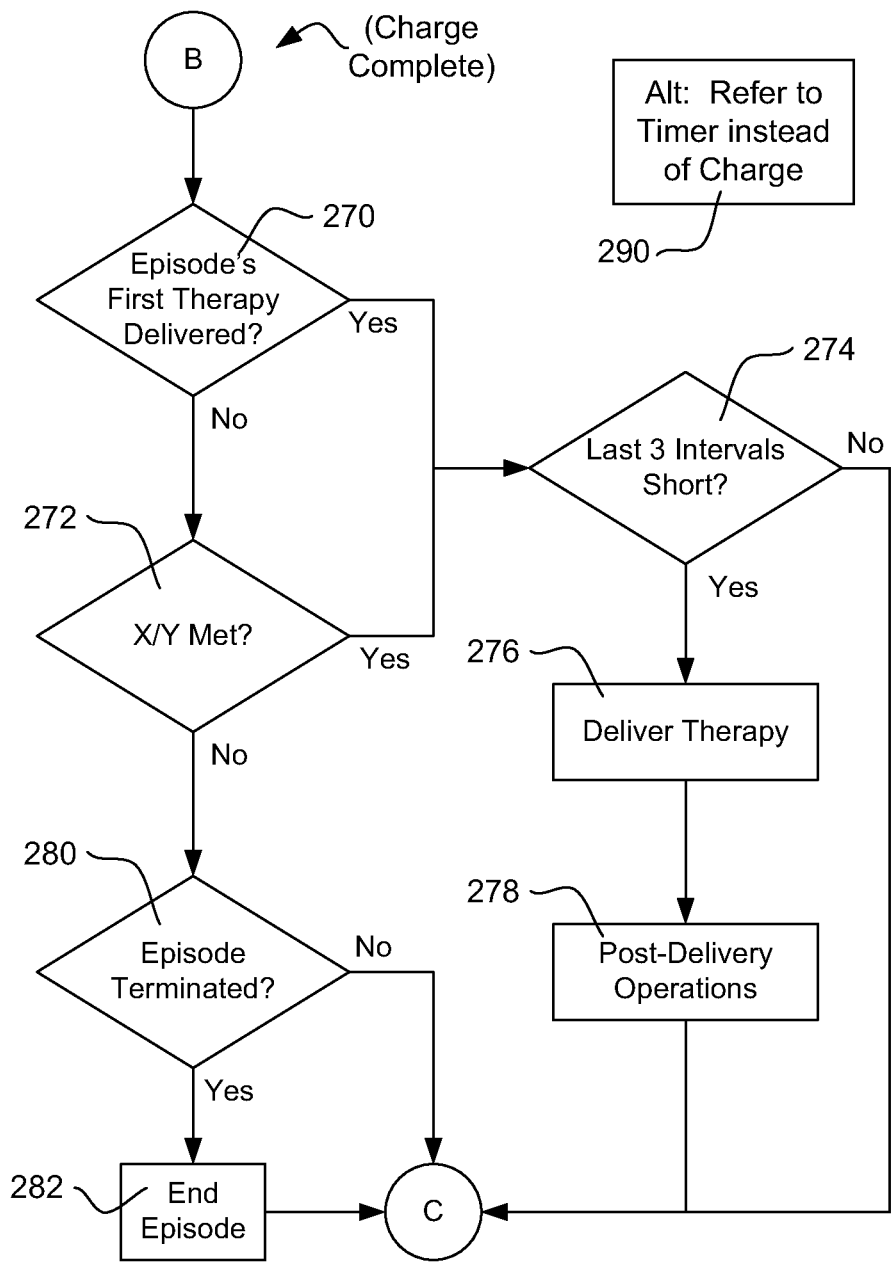

FIGS. 7A-7B show a process flow for another illustrative method for managing therapy delivery. At a summary level, the example of FIGS. 7A-7B relies on factors related to an X/Y counter to determine whether to make an initial identification of a treatable condition and, following initial identification of a treatable condition, the X/Y counter is cleared and new data refills the X/Y counter, ensuring that the arrhythmic condition is continuing before therapy is delivered FIGS. 7A-7B show various conditional steps using "Charge" states; in another example, a timer may be referenced instead, as noted at 290. In yet another example, rather than a timer, a selected number of detected events must occur while the ICSD waits to declare itself ready for therapy.

The method begins in FIG. 7A at an event detection block 250, which responds to events detected in a sensed cardiac signal. When an event is detected at 250, the method proceeds to beat analysis at 252. Beat analysis 252 may include, for example, any suitable noise-identification analysis and/or analysis to identify double detection or other detection anomalies.

If beat analysis 252 fails (indicating that the detected event is not likely a cardiac event of a desired type), the method returns to 250. If beat analysis passes, the method goes to block 254, where the X/Y counter is adjusted according to the beat analysis 252. This may integrate features associated with rate and/or morphology analysis to determine whether a detected event indicates a benign cardiac state or a treatable condition.

Next, the method determines whether charging has already begun, as indicated at 256. If so, the method continues to block 258, which determines whether charging is complete. If charging is complete, the method goes to FIG. 7B, via "B". In the alternative 290, the method would determine whether a therapy delay timer has started and, if so, whether the timer has expired at blocks 256 and 258, respectively.

If charging has started but is not complete, the method next determines whether the arrhythmia has reverted to benign rhythm and the episode can end, as shown at 260. If the arrhythmia has reverted, various steps can be taken to end the episode, for example, data stored in temporary memory may be written to a memory storage location for later retrieval, and the defibrillation capacitor (if it was charging) may be discharged. Any suitable adjustments that are desired following a non-sustained event may be made as well, for example, by adjusting persistence criteria. After block 262, or if the arrhythmia has not reverted at 260, the method goes to "A", which leads back to beat detection 250.

Returning to block 256, if charging has not already begun (or the therapy timer has not started), the method continues to block 264, where the contents and history of the X/Y counter are analyzed to determine whether charging should begin (or the therapy timer should start). If not, the method again goes to "A", which leads back to beat detection 250.

If block 264 finds that charging should begin, then charging is initiated, as shown at 266, which may include sending or recording a charge begin marker (used at 256), or declaring that an episode has begun. In the alternative 290, a therapy timer can be initialized at block 264.

In the illustrative example, once charging is initiated at block 266, the X/Y counter is cleared, as shown at 268. In some examples, this means emptying the X/Y counter completely; while in other embodiments the X/Y counter may be set to some predetermined initial condition for the post-charge-begin analysis. For example, the X/Y counter may be a 20 event counter (that is, Y=20) and "clearing" at block 268 could set X to zero, ten, or some other predetermined value. In the alternative 290, if/when the therapy timer is initialized, the X/Y counter would be cleared. Following block 268, the method goes to "A" and returns to beat detection 250.

Turning to FIG. 7B, after charging is complete (at 258), (and/or, using the alternative 290, if the therapy timer has expired) the illustrative method next determines whether a first therapy in the present episode has been delivered already, as shown at 270. If not, then the method determines whether the X/Y criteria has been met after the charge begin and data clearing steps at 266 and 268 (FIG. 7A). In another alternative example, a therapy timer may be omitted after the first therapy is delivered in an episode, or a therapy timer may be selectively applied when only certain therapies are being considered for example in a system configured to apply multiple different therapies in a predetermined order or in response to particular conditions.

The thresholds applied before and after charge initiation in the method of FIGS. 7A-7B may be different from one another in some embodiments. The following combinations are illustrative of X/Y thresholds that can be used in the illustrative example:

Initial ID X/Y=18/24, with variable Persistence; Confirmation Criteria X/Y=12/16, No Persistence.

Initial ID X/Y=12/16, variable persistence; Confirmation Criteria X/Y=10/16, No Persistence.

Initial ID X/Y=18/24 (up to 30/40), variable Persistence; Confirmation Criteria X/Y=12/18, no persistence.

In these examples, Persistence refers to requiring the X/Y ratio to be shown for a series of M consecutive calculations, Static Persistence calls for M to be fixed, and Variable Persistence indicates that M can be increased/extended if a non-sustained tachycardia is identified. Other values than those shown may be used. Alternatively, the same criteria is reapplied after charge begin. These examples may be characterized as offering an initial identification criteria and a confirmation criteria.

If the X/Y rule(s) are met at 272, the method optionally applies a "last three interval" rule as shown at 274, in which the last three intervals (raw, noise-detection-passing, or even certified by overcounting detection methods, depending on which of several embodiments is used) are analyzed to determine whether each is short. If the last three interval rule is not met, the method continues back to block 250 in FIG. 7A via "C". If the last three interval rule is met, the method delivers therapy, as shown at 276.

The last three interval rule may be applied if the first therapy of the episode has already been delivered, advancing from block 270 as shown. In another embodiment, the last three interval rule can be applied between blocks 270 and 276, but is omitted between blocks 272 and 276. Rather than "last three," a last-one, last-two or other number of intervals may be checked, and, if desired, this embodiment may be combined with the embodiment of FIG. 4, in which the number of intervals checked in the "last three" rule increases in response to indications of benign cardiac activity.

Following therapy delivery, any suitable post-therapy-delivery operations are performed as indicated at 278. Some examples of post-therapy-delivery operations 278 may include blanking, manipulating switches to eliminate afterpotentials, and, if desired, additional filtering of incoming signal to remove DC afterpotentials or to remedy baseline drift that may occur during and following therapy delivery. Post-therapy pacing can also be provided in appropriate circumstances, for example, as needed following defibrillation or cardioversion therapy. The method returns to FIG. 7A via "C".

Returning to block 272, if the X/Y criteria is not met when reapplied, the method next determines whether the episode has terminated, as shown at 280. In one example, the episode is considered terminated if the calculated rate drops below a predetermined threshold. In another example, the episode is not considered terminated until the calculated rate drops below a predetermined threshold for a set number of calculations of the rate. For example, the treatable arrhythmia may be considered terminated when the detected event rate drops below 140 BPM for 24 consecutive calculations. Other thresholds for determining that the episode has ended may be applied in other embodiments. For example, the rate threshold may be a programmable feature. If the episode has terminated at 240, then End of Episode activities are performed as shown at 282. The End of Episode activities may be as described above. The method again returns to FIG. 7A from either of block 240 or 242 via "C".

Figure 8:
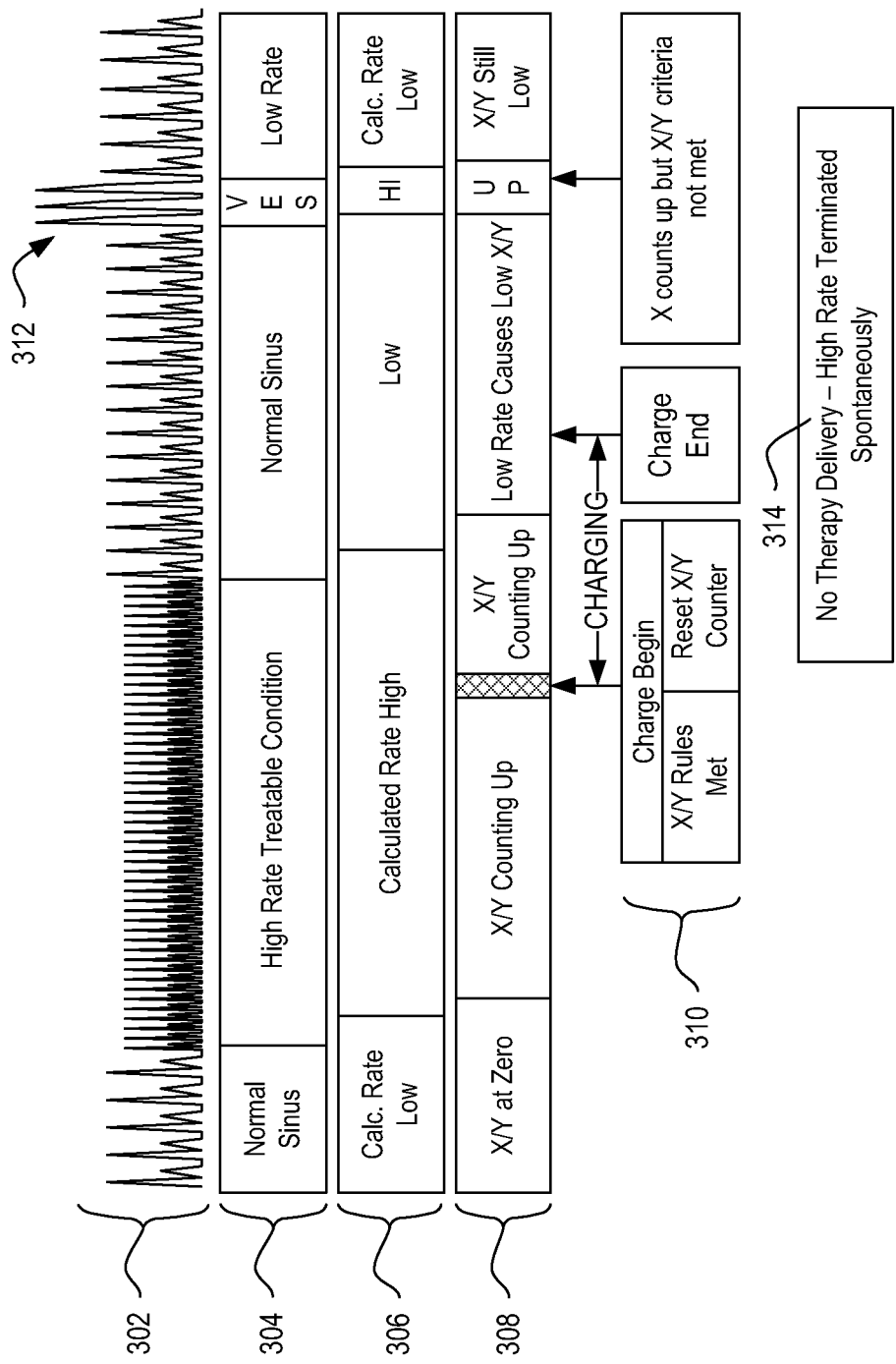
FIG. 8 illustrates analysis using the method of FIGS. 7A-7B.

FIG. 8 illustrates analysis using the method of FIGS. 7A-7B. A representation of a cardiac signal is shown at 302, and characterized at 304. The patient can be seen to transition from a low rate or normal rhythm to VT, with spontaneous reversion to a low rate condition. A series of VES occurs as shown at 312. The calculated rate is characterized as shown at 306, and the status/contents of an X/Y counter are shown at 308. During the low rate rhythm, the rate 306 is low, and the X/Y counter 308 is either Off or Low. When VT starts, the rate 306 goes High, and the X/Y counter 308 begins counting up toward its threshold. Once the X/Y counter is met and an optional persistence factor is satisfied, the ICSD has an initial identification of a treatable condition. The initial treatable condition is addressed in the illustrative system by beginning to charge a therapy capacitor, as shown at 310.

As also shown at 310, when charging begins, the X/Y counter is reset to zero. During charging, the X/Y counter begins to fill again with indications of Treatable and benign cardiac events. Once charging is completed, the system analyzes the contents of the X/Y counter to determine whether an X/Y counter condition is met. As indicated, a counter requirement can be applied (confirmation criteria of 10/15, for example) for confirmation than is used in the initial treatable condition determination (X/Y criteria of 14/18, for example), and persistence may be reduced in the illustrative example from three (charge criteria), to zero (therapy criteria).

If the Confirmation criteria is satisfied, therapy will be delivered. However, in the example shown, the VT that led to initiation of charging spontaneously ends and the cardiac rhythm returns to a slow rate condition. As a result, the X/Y criteria is not met when charging ends. A VES triplet is shown at 312. Because the VES may be of a different amplitude or shape than other signals, overcounting can occur and/or may be difficult to resolve, leading to a series of short intervals. This momentarily causes the calculated rate to increase and the X/Y counter may start to increment. However, the fast detections do not persist long enough in this example to meet the confirmation criteria being applied via the X/Y counter. As a result, no therapy is delivered, as noted at 314.

As with other examples herein, rather than starting to charge a therapy capacitor in response to the initial treatable condition being identified, the ICSD may initialize a therapy timer or perform different steps to prepare for therapy delivery. In another example, because the X/Y counter is being refilled, no timer is needed and, instead, the X/Y counter is cleared and if, as the X/Y counter fills, it again indicates a treatable condition within a predetermined period of time (for example, one minute), therapy is delivered.

It should be noted that the description "preparing to deliver therapy" in response to an initial identification of a treatable condition can include any number of different operations by the ICSD. For example, after an initial identification of a treatable condition, an ICSD can prepare to deliver therapy by one or more of: providing annunciation to the patient; attempting external communication (communication with a programmer, bedside monitor, cellular network, etc.); charging a capacitor; recording signal data; measuring device parameters such as battery capacity; identifying time windows for therapy delivery; performing sub-threshold testing of therapy delivery vectors; observing patient impedance characteristics; measuring noncardiac signal noise; or performing any other desired function. Depending upon the particular embodiment, these functions can continue until one or more of the following occur: a therapy capacitor reaches a target voltage/energy; a timer expires; and/or a predetermined number of detected events occur, or any other suitable condition indicating that the ICSD is ready to deliver therapy occurs. For some systems and devices, simply waiting for expiration of a timer is a preparation for therapy insofar as such delays can help ensure that non-sustained, transient conditions do not cause inappropriate therapy.

In another embodiment, an X/Y counter is used to analyze a window of data to identify a treatable condition. Upon initiation of charging, the values in the X/Y counter are stored (rather than cleared as in FIGS. 7A-7B and 8), and analysis continues during charging, filling the X/Y counter with new data. When charging is complete, the status of the X/Y counter is compared to the status stored at the time charging was initiated. In the example, therapy would be delivered either immediately if the X/Y counter indicates a treatable condition that is at least as hazardous as that which existed at the time of charge initiation or once the X/Y counter reaches a status that is at least equivalent to that which occurred at the time of charge initiation. Once again, persistence may be omitted when performing the confirmation analysis of the X/Y counter.

For example, if charging is called using a persistence=3 factor and an X/Y threshold of 18/24 (18 Treatable out of 24 events), charging may begin at X/Y=21/24. At the end of the charging process, the system would then observe whether X/Y is greater than or equal to 21/24 at least once in order to trigger therapy delivery. If desired, a maximum X value (such as 22) may be set relative to Y, to ensure that application of a persistence rule does not lead to X/Y=24/24, which could be difficult to reach if the patient has any undersensing.

The above illustrative examples show several systems and methods in which cardiac activity is monitored after charging starts. In some examples, if slow rate or normal cardiac events are detected after charging starts, additional therapy criteria are applied before a therapy will be delivered. In this fashion, a patient who displays some indications of benign cardiac activity during and following charging is rendered less likely to receive unnecessary therapy in response to a self-terminating arrhythmia.

In some examples, tiered analysis can be applied, having episode declaration criteria applied first, followed by therapy delivery criteria, and methods as shown above may be used to affect the therapy delivery criteria subsequent to the episode declaration criteria, with or without a delay period intervening. Several of the above examples make note of a delay period during which capacitor charging occurs to prepare for therapy delivery. Not all systems or therapies will require such a delay period; for example, if ATP is to be applied, therapy delivery may be available with no or very minimal delay period.

Figure 9:
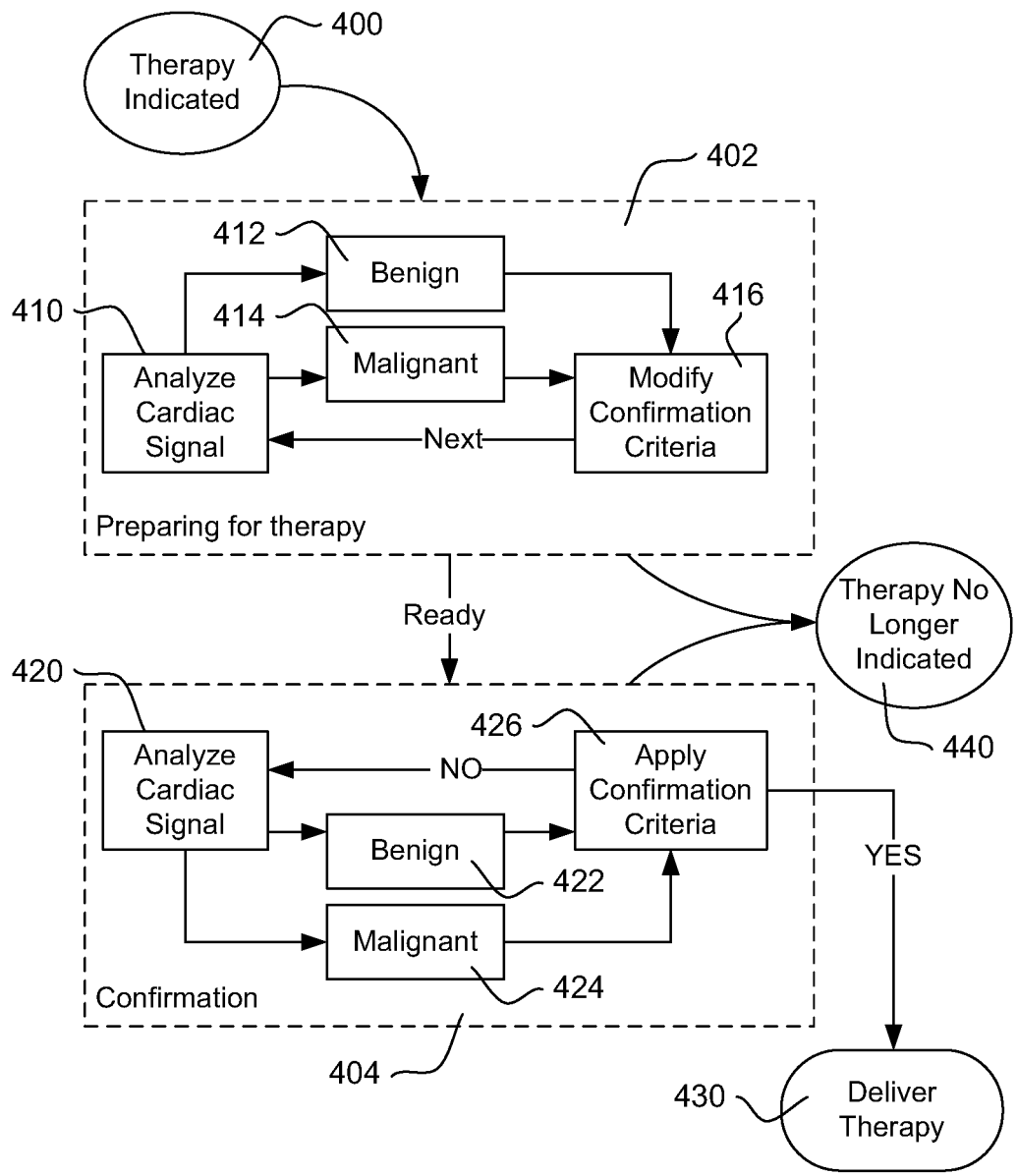
FIG. 9 is a block diagram for an illustrative method.

FIG. 9 is a block diagram for an illustrative method. The method can be performed in an ICSD that senses cardiac signals from implanted electrodes in order to determine whether a treatable cardiac arrhythmia is occurring. In response to an initial identification of treatable cardiac arrhythmia, the ICSD may prepare to deliver therapy, for example, by charging high power capacitors to prepare to deliver therapy to a recipient of the ICSD.

As indicated at 400, the method begins with a determination that therapy is indicated. Determinations that therapy is indicated may be made by any method in this example. Once therapy is indicated, the method operates in a "Preparing for Therapy" block 402, until the ICSD is ready to deliver therapy, at which time the method operates in a "Confirmation" block 404. The methods are shown at 410-412/414-416 and 420-422/424-426, and may be performed within larger processes, in parallel to other methods, or in addition to other processes including, for example, event detection.

The cardiac signal is analyzed at 410 and characterized as one of benign 412 or treatable 414. Once the cardiac signal is characterized, as shown at 416, the method may modify "Confirmation criteria." In this example, Confirmation criteria refers to thresholds, standards or analysis used to determine whether a treatable cardiac arrhythmia is ongoing, in order to confirm that therapy should be delivered once the ICSD is ready. Several examples have been discussed above.

In an illustrative example, when the cardiac signal is characterized as benign 412, the Confirmation criteria are modified such that a greater quantity of cardiac signal indicating a treatable arrhythmia is required to confirm therapy delivery. In some examples, this may include modifying the Confirmation criteria by increasing the number of morphologically treatable events or short intervals are needed to confirm therapy. In another example, rather than an event driven system, a system that analyzes blocks of time (for example, 1 second, 3 second, or other duration blocks of time, which may be separate, adjacent or overlapping in several embodiments) for cardiac rhythm analysis may add to the number or length of such time blocks. Next, the method loops back to cardiac signal analysis 410.

Once the ICSD is ready for therapy, a transition is made to block 404, in which cardiac signal is analyzed at 420 and characterized as benign 422 or treatable 424. Using these characterizations, the Confirmation criteria are applied at 426 in order to determine whether a treatable cardiac arrhythmia is ongoing. If a treatable cardiac arrhythmia is ongoing, therapy is confirmed and therefore delivered as shown at 430. Otherwise, the method loops back to analyze cardiac signal 420.

If it is determined that therapy is no longer indicated during analysis in either of block 402 or 404, such a determination is made as shown at 440. If therapy is no longer indicated, then the system may perform various methods following identification of a non-sustained treatable arrhythmia. These may include storing data related to a non-sustained arrhythmia, annunciating potential sensing difficulties based on identification of non-sustained arrhythmia(s), changing sensing vectors, methods or thresholds, and/or performing any cleanup or safety tasks necessitated by the aborted therapy.

Modifying the duration of analysis or adding more events to event-based analysis may be considered ways of making existing analysis more or less rigorous. In another illustrative example, the Confirmation criteria may be modified by changing the character of analysis or adding an extra layer of analysis, rather than making existing analysis more rigorous. In some embodiments, the Confirmation criteria may use several tiers of analysis such as a first tier that relies on consecutive-short-intervals, a second tier that relies on morphology analysis such as correlation to a Normal Sinus template, and a third tier that relies on analyzing an additional sensing vector to confirm treatable arrhythmia. In a tiered Confirmation criteria embodiment, the default may be to rely on only a first tier of analysis for therapy confirmation and, if cardiac signals are characterized as benign, a second tier of analysis may be enabled, and if further cardiac signals are characterized as benign, the third tier of analysis may be enabled. In some such embodiments, the additional tiers of analysis may be called with or without modifications to the first tier of analysis, or the additional tiers may be called to replace the first tier of analysis. In some embodiments, any added tiers may be disabled in response to characterization of cardiac signals as treatable.

While not shown in the above examples, the initiation of charging may be accompanied by a blanking period of a few hundred milliseconds, if desired, to avoid sensing artifacts that may occur in some systems with charge initiation. Systems may also mitigate such noise through filtering or avoid such noise by design of the charging circuit in addition to or in place of blanking. As noted, not all systems/methods rely on charging as a factor in the setting of thresholds for confirmation.

Some examples above use a four interval average to estimate cardiac event rate. Other sample sizes, for example from 1-20 events may be used instead, or even larger groups, if desired. Larger sets may provide smoother calculations, while smaller sets may be more responsive to onset of different rhythms and sudden rate changes.

U.S. Pat. No. 7,330,757, titled METHOD FOR DISCRIMINATING BETWEEN VENTRICULAR AND SUPRAVENTRICULAR ARRHYTHMIAS, U.S. Pat. No. 7,248,921, titled METHOD AND DEVICES FOR PERFORMING CARDIAC WAVEFORM APPRAISAL, US Patent Application Publication Number 2009-0259271, titled METHODS AND DEVICES FOR ACCURATELY CLASSIFYING CARDIAC ACTIVITY, and US Patent Application Publication Number 2010-0004713, titled METHODS AND DEVICES FOR ACCURATELY CLASSIFYING CARDIAC ACTIVITY, are each incorporated herein by reference as providing illustrative examples of implantable cardiac stimulus systems and associated methods of implant, analysis and therapy. Reference to patents and applications is not intended as limiting, and other methods may be used instead of or in addition to any of these examples in other embodiments.

Various ranges for therapy delivery energy are known and are often presented in terms of delivered energy. Ranges for therapy delivery energy may include, for example, ranges from 0.1 Joules to 35 or more Joules for transvenous and/or epicardial systems, and sometimes higher ranges for subcutaneous therapy delivery, for example, 0.1 Joules up to or in excess of 40, 65, 80 or 100 Joules. Patient anatomy and the location of therapy delivery electrodes can impact the energy required for effective therapy. The present invention may be used in systems directed at treating arrhythmias occurring in one or more of the ventricles and/or atria of a patient. In some examples, atrial flutter or atrial fibrillation may be treated.

Those skilled in the art will recognize that the present invention may be manifested in a variety of forms other than the specific embodiments described and contemplated herein. Accordingly, departures in form and detail may be made without departing from the scope and spirit of the present invention.

What is claimed is:

1. A method of operation in an implantable cardiac stimulus device (ICSD) comprising a housing that contains a power source and operational circuitry that operates by analyzing cardiac signals from implanted electrode(s) in order to determine whether a treatable arrhythmia is detected, the method comprising:
the ICSD making an initial determination that a treatable condition is occurring and in response:
the ICSD initializing a confirmation counter storing a Confirmation Value to an Initial Confirmation Value; and
the ICSD initiating preparation for therapy delivery;
after initiating preparation for therapy delivery and before therapy delivery, the ICSD detecting a plurality of heart beats and determining whether the heart beats indicate that a benign cardiac rhythm has resumed;
for a plurality of heart beats detected after the ICSD has initiated preparation for therapy delivery, adjusting the Confirmation Value as follows:
if the heart beat indicates that a benign cardiac rhythm has resumed, incrementing the Confirmation Value counter unless it is at a Maximum Value;
if the heart beat does not indicate that a benign cardiac rhythm has resumed, decrementing the Confirmation Value counter unless it is at a Minimum Value;
following completion of preparations for therapy delivery, perform the following:
a) initializing a Shockable Beat counter to an Initial Shock Value, wherein the Shockable Beat counter is for tracking consecutive detected heart beats that indicate therapy is needed and the Initial Shock Value is either zero or is set based on a series of previously detected events;
b) detecting a heart beat and determining whether the heart beat indicates therapy is needed or that benign cardiac rhythm has resumed and:
if the heart beat indicates therapy is needed, incrementing the Shockable Beat counter, and decrementing the Confirmation value counter unless it is already at the Minimum Value;
if the heart beat indicates benign cardiac rhythm has resumed, resetting the Shockable Beat counter to zero and incrementing the Confirmation Value counter unless it is already at the Maximum Value;
c) after step b), comparing the Shockable Beat counter to the Confirmation Value counter and:
if the Shockable Beat counter is equal to or greater than the Confirmation Value counter, the ICSD proceeding to deliver therapy to the patient; or
if the Shockable Beat counter is not equal to or greater than the Confirmation Value counter, the ICSD either determining that therapy is no longer indicated for the patient or returning to step b).

2. The method of claim 1 wherein preparation for therapy delivery comprises charging an output capacitor to a therapy level for delivery of therapy.

3. The method of claim 1 wherein preparation for therapy delivery comprises waiting for a timer to expire after the initial determination and before delivering therapy.

4. The method of claim 1 wherein preparation for therapy delivery comprises waiting for a predetermined number of cardiac events to be detected after the initial determination and before delivering therapy.

5. The method of claim 1 wherein a heart beat indicates that a benign cardiac rhythm has resumed if a cardiac rate slower than a slow-rate threshold is calculated using data related to the heart beat.

6. The method of claim 1 wherein a heart beat indicates that a benign cardiac rhythm has resumed if it matches a stored template for a benign cardiac rhythm.

7. The method of claim 1 wherein a heart beat indicates that a benign cardiac rhythm has resumed if it shows low beat-to-beat variability in comparison to one or more adjacent-in-time heart beats.

8. The method of claim 1 wherein a heart beat indicates that a benign cardiac rhythm has resumed if it has a narrow width.

9. The method of claim 1 wherein the Initial Shock Value is set based on the series of previously detected events, which includes assessing a quantity of heart beats detected just prior to completion of Therapy Preparation and setting the Initial Shock Value to the number of such heartbeats that indicate therapy is needed.

10. The method of claim 9 wherein the quantity of heart beats is three, and the Minimum Value for the Confirmation Value counter is three.

11. An implantable cardiac stimulus device (ICSD) comprising a housing that contains a power source and operational circuitry that operates by analyzing cardiac signal data from implanted electrodes in order to determine whether a treatable arrhythmia is detected, wherein the operational circuitry is configured to perform a method of verifying therapy delivery comprising:
the ICSD making an initial determination that a treatable condition is occurring and in response:
the ICSD initializing a confirmation counter storing a Confirmation Value to an Initial Confirmation Value; and
the ICSD initiating preparation for therapy delivery;
after initiating preparation for therapy delivery and before therapy delivery, the ICSD detecting a plurality of heart beats and determining whether the heart beats indicate that a benign cardiac rhythm has resumed;

for a plurality of heart beats detected after the ICSD has initiated preparation for therapy delivery, adjusting the Confirmation Value as follows:
  if the heart beat indicates that a benign cardiac rhythm has resumed, incrementing the Confirmation Value counter unless it is at a Maximum Value;
  if the heart beat does not indicate that a benign cardiac rhythm has resumed, decrementing the Confirmation Value counter unless it is at a Minimum Value;
following completion of preparations for therapy delivery, performing the following:
a) initializing a Shockable Beat counter to an Initial Shock Value, wherein the Shockable beat counter is for tracking consecutive detected heart beats that indicate therapy is needed and the Initial Shock Value is either zero or is set based on a series of previously detected events;
b) detecting a heart beat and determining whether the heart beat indicates therapy is needed or that benign cardiac rhythm has resumed and:
  if the heart beat indicates therapy is needed, incrementing the Shockable Beat counter, and decrementing the Confirmation value counter unless it is already at the Minimum Value;
  if the heart beat indicates benign cardiac rhythm has resumed, resetting the Shockable Beat counter to zero and incrementing the Confirmation Value counter unless it is already at the Maximum Value;
c) after step b), comparing the Shockable Beat counter to the Confirmation Value counter and:
  if the Shockable Beat counter is equal to or greater than the Confirmation Value counter, the ICSD proceeding to deliver therapy to the patient; or
  if the Shockable Beat counter is not equal to or greater than the Confirmation Value counter, the ICSD either determining that therapy is no longer indicated for the patient or returning to step b).

12. The ICSD of claim 11 wherein the operational circuitry includes:
an output capacitor and a charger coupled to the output capacitor such that the output capacitor can be charged by the charger to temporarily store therapeutic energy prior to delivering therapy;
input circuitry for receiving input signals from the implanted electrodes and amplifying and filtering the input signals;
a controller coupled to the input circuitry, output capacitor, output circuitry, and charger and controlling the functions thereof, the controller configured to determine whether a treatable arrhythmia is detected and to perform the method of verifying therapy delivery; and
a battery providing power to the operational circuitry.

13. The ICSD of claim 12 wherein the operational circuitry is configured such that preparation for therapy comprises charging the output capacitor to a therapy level for delivery of therapy.

14. The ICSD of claim 11 wherein the operational circuitry is configured such that preparation for therapy comprises waiting for a timer to expire after the initial determination and before delivering therapy.

15. The ICSD of claim 11 wherein the operational circuitry is configured such that preparation for therapy comprises waiting for a predetermined number of cardiac events to be detected after the initial determination and before delivering therapy.

16. The ICSD of claim 11 wherein the operational circuitry is configured such that a heart beat indicates that a benign cardiac rhythm has resumed if it matches a stored template for a benign cardiac rhythm.

17. The ICSD of claim 11 wherein the operational circuitry is configured such that a heart beat indicates that a benign cardiac rhythm has resumed if it shows low beat-to-beat variability in comparison to one or more adjacent-in-time heart beats.

18. The ICSD of claim 11 wherein the operational circuitry is configured such that a heart beat indicates that a benign cardiac rhythm has resumed if it has a narrow width.

19. The ICSD of claim 11 wherein the operational circuitry is configured such that the Initial Shock Value is set based on the series of previously detected events, which includes assessing a quantity of heart beats detected just prior to completion of Therapy Preparation and setting the Initial Shock Value to the number of such heartbeats that indicate therapy is needed.

20. The ICSD of claim 19 wherein the operational circuitry is configured such that the quantity of heart beats is three, and the Minimum Value for the Confirmation Value counter is three.

* * * * *